(12) United States Patent
Parker et al.

(10) Patent No.: US 12,593,983 B2
(45) Date of Patent: Apr. 7, 2026

(54) INTERFEROMETRIC NEAR INFRARED SPECTROSCOPY SYSTEM

(71) Applicant: COMIND TECHNOLOGIES LIMITED, London (GB)

(72) Inventors: William Parker, London (GB); Dawid Borycki, London (GB); Amrit Lotay, London (GB); Tanja Dragojevic, London (GB)

(73) Assignee: CoMind Technologies Limited, London (GB)

( * ) Notice: Subject to any disclaimer, the term of this patent is extended or adjusted under 35 U.S.C. 154(b) by 0 days.

(21) Appl. No.: 19/106,543

(22) PCT Filed: Aug. 25, 2023

(86) PCT No.: PCT/GB2023/052217
§ 371 (c)(1),
(2) Date: Feb. 25, 2025

(87) PCT Pub. No.: WO2024/042339
PCT Pub. Date: Feb. 29, 2024

(65) Prior Publication Data
US 2026/0000298 A1     Jan. 1, 2026

(30) Foreign Application Priority Data

Aug. 26, 2022    (GB) ...................................... 2212442

(51) Int. Cl.
*A61B 5/00*          (2006.01)
*G16H 40/63*        (2018.01)
(52) U.S. Cl.
CPC .......... *A61B 5/0075* (2013.01); *A61B 5/0042* (2013.01); *G16H 40/63* (2018.01); *A61B 2562/223* (2013.01); *A61B 2576/026* (2013.01)

(58) Field of Classification Search
CPC ................ A61B 5/0075; A61B 5/0042; A61B 2562/223; A61B 2576/026; G16H 40/63
See application file for complete search history.

(56) References Cited

U.S. PATENT DOCUMENTS

2019/0053721 A1*   2/2019   Boas .................... A61B 5/0261
2019/0336060 A1*  11/2019  Shen .................. G01B 9/02091

FOREIGN PATENT DOCUMENTS

WO        2022084700        4/2022
WO        2022115643        6/2022

OTHER PUBLICATIONS

International Search Report from corresponding PCT application No. PCT/GB2023/052217 (Nov. 16, 2023).

(Continued)

*Primary Examiner* — Keith M Raymond
*Assistant Examiner* — Adam D. Kolkin
(74) *Attorney, Agent, or Firm* — Barnes & Thornburg

(57)     ABSTRACT

An interferometric near infrared spectroscopy, iNIRS, system comprising: a light emitting arrangement comprising a light source configured to provide wavelength swept emission of light; and a light detecting arrangement comprising an interferometric optical detector; the iNIRS system comprising a plurality of optical channels arranged to define; a first optical channel path arranged to extend: (i) between the light source and the object for delivering first sample light from the light source to the object, and (ii) between the object and the detector for delivering first sample light received from the object to the detector; a second optical channel path arranged to extend: (i) between the light source and the object for delivering second sample light from the light source to the object, and (ii) between the object and the detector for delivering second sample light received from the object to the detector; and a reference optical channel path arranged to extend between the light source and the (Continued)

detector for delivering reference light from the light source
to the detector along a reference channel.

20 Claims, 3 Drawing Sheets

(56)                References Cited

OTHER PUBLICATIONS

Kholiqov, et al., "Interferometric near-infrared spectroscopy (iNIRS):
performance tradeoffs and optimization", Optics Express, 2017, vol.
25, No. 23, pp. 1-22.
Search Report from corresponding GB patent application No.
682212442.4 (Feb. 14, 2023).

* cited by examiner

INTERFEROMETRIC NEAR INFRARED SPECTROSCOPY SYSTEM

CROSS-REFERENCE TO RELATED APPLICATIONS

This application is a US national stage application under Section 371 of PCT Application No. PCT/GB2023/052217, filed on Aug. 25, 2023, which claimed priority from United Kingdom Patent Application No. GB 2212442.4, filed on Aug. 26, 2022, the contents of which are each incorporated by reference herein in their entireties.

TECHNICAL FIELD

The present disclosure relates to the field of interferometric near infrared spectroscopy ('iNIRS') systems. For example, such an iNIRS system may be provided for neuroimaging and analysis.

BACKGROUND

Near infrared spectroscopy ('NIRS') is a spectroscopic method which uses the near infrared region of the electromagnetic spectrum (e.g. between 700 and 2500 nm). NIRS systems can be used to provide non-invasive monitoring of scattering and absorption properties of a medium. Radiation at NIRS wavelengths is less easily absorbed by human skin (and also bones) than visible light, and so NIRS radiation may penetrate both skin and skull, and penetrate into brain tissue. NIRS may be used as a technique for non-invasive imaging of human brain tissue by monitoring scattering and absorption properties of the NIRS radiation within the brain tissue.

While NIRS methods can be extended for monitoring oxygenation, when multiple wavelengths are used, the blood flow monitoring is necessary to infer information about metabolism. Diffuse correlation spectroscopy (DCS) can be used to noninvasively monitor blood flow in the brain by measuring temporal fluctuations of the light re-emitted from the sample. DCS can further extract other brain metrics, including intracranial pressure (ICP). However, to extract flow, existing DCS approaches require additional devices, and heavy averaging, making the final approach bulky and slow. Also, to quantify the blood flow DCS requires optical properties, which usually are assumed or achieved from the separate NIRS instrument. Finally, since DCS and NIRS relies only on the light intensities, they reject half of the information about the scattered light, encoded in the optical phase. Consequently, measurements are affected by additional assumptions from disregarding phase information.

It is thus desirable to provide improved technology for neuromonitoring and analysis, which will combine NIRS and DCS into a single modality, and rapidly provide optical and dynamical properties of the biological tissues.

SUMMARY

Aspects of the disclosure are set out in the independent claims and optional features are set out in the dependent claims. Aspects of the disclosure may be provided in conjunction with each other, and features of one aspect may be applied to other aspects.

In an aspect, there is provided an interferometric near infrared spectroscopy, iNIRS, system comprising: a light emitting arrangement comprising a light source configured to provide wavelength swept emission of light; and a light detecting arrangement comprising an interferometric optical detector. The iNIRS system comprises a plurality of optical channels arranged to define: a first optical channel path arranged to extend: (i) between the light source and the object for delivering first sample light from the light source to the object, and (ii) between the object and the detector for delivering first sample light received from the object to the detector; a second optical channel path arranged to extend: (i) between the light source and the object for delivering second sample light from the light source to the object, and (ii) between the object and the detector for delivering second sample light received from the object to the detector; and a reference optical channel path arranged to extend between the light source and the detector for delivering reference light from the light source to the detector along a reference channel. The detector is arranged to combine: the reference light with the first sample light to provide light signals at a plurality of first beat frequencies between the first sample light and the reference light; and the reference light with the second sample light to provide light signals at a plurality of second beat frequencies between the second sample light and the reference light. The first optical channel path is of a different length to the second optical channel path to inhibit spectral overlap between the first and second beat frequencies.

Embodiments may enable the detector to provide a single interferogram which contains two, separate, beat frequency distributions. The two beat frequency distributions may be separated out and used to provide two separate time of flight distributions for photons of sample light. Digital processing may be performed on both of these distributions to provide imaging of the object. Embodiments may enable more data to be obtained for each measurement cycle. Embodiments may also enable more data to be obtained without needing additional signal processing circuitry. For example, more sample light photon time of flight distributions may be obtained from each single digitiser channel of an analogue to digital converter.

The iNIRS system is arranged so that there are two or more optical paths that photons of sample light can take through optical channels of the iNIRS system. That is, the system is arranged so that sample light photons emitted from the light source and received at the detector could have travelled two or more different routes, e.g. through two or more different portions of optical channel (irrespective of the path they took through the object to be imaged). For example, the iNIRS system may comprise at least one of: (i) two different sample delivery channels for coupling the light source to the object to be imaged, and (ii) two different sample receiving channels for coupling the object to be imaged to the detector. The difference in optical channel path length may be provided by having one of the sample delivery channels be of a different length to the other sample delivery channel, and/or one of the sample receiving channels be of a different length to the other sample receiving channel. For example, the iNIRS system may comprise two sample delivery channels and two sample receiving channels, with one sample delivery channel longer than the other, and one sample receiving channel longer than the other. Each different optical channel path may comprise a different combination of sample delivery channel(s) and sample receiving channel(s) through which light may travel between the source and detector.

One such aspect of the present disclosure may provide an interferometric near infrared spectroscopy, iNIRS, system comprising: a light emitting arrangement comprising: a light source configured to provide wavelength swept emission of light; a sample delivery channel coupled to the light source and arranged to be coupled to an object to be imaged for directing light from the light source towards the object; and a reference channel coupled to the light source for receiving light therefrom; a light detecting arrangement comprising: a first sample receiving channel arranged to be coupled to the object for receiving first sample light therefrom; a second sample receiving channel arranged to be coupled to the object for receiving second sample light therefrom, the first and second sample light each comprising light emitted from the light source; and an interferometric optical detector coupled to: (i) the first sample receiving channel for receiving first sample light, (ii) the second sample receiving channel for receiving second sample light, and (iii) the reference channel for receiving reference light. The optical detector is arranged to combine: the reference light with the first sample light to provide light signals at a plurality of first beat frequencies between the first sample light and the reference light; and the reference light with the second sample light to provide light signals at a plurality of second beat frequencies between the second sample light and the reference light. The first sample receiving channel is of a different length to the second sample receiving channel to inhibit spectral overlap between the first and second beat frequencies.

Another such aspect of the present disclosure may provide an interferometric near infrared spectroscopy, iNIRS, system comprising: a light emitting arrangement comprising: a light source configured to provide wavelength swept emission of light; a first sample delivery channel coupled to the light source and arranged to be coupled to an object for directing light from the light source towards the object; a second sample delivery channel coupled to the light source and arranged to be coupled to the object for directing light from the light source towards the object; and a reference channel coupled to the light source for receiving light therefrom; a light detecting arrangement comprising: a sample receiving channel arranged to be coupled to the object for receiving first and second sample light therefrom, the first sample light comprising light emitted from the light source which travelled along the first sample delivery channel and the second sample light comprising light emitted from the light source which travelled along the second sample delivery channel; and an interferometric optical detector coupled to: (i) the sample receiving channel for receiving first and second sample light, and (ii) the reference channel for receiving reference light. The optical detector is arranged to combine: the reference light with the first sample light to provide light signals at a plurality of first beat frequencies between the first sample light and the reference light; and the reference light with the second sample light to provide light signals at a plurality of second beat frequencies between the second sample light and the reference light. The first sample delivery channel is of a different length to the second sample delivery channel to inhibit spectral overlap between the first and second beat frequencies.

Such examples may provide iNIRS systems in which two (or more) optical channel paths are defined (whether by using two or more sample delivery channels and/or two or more sample receiving channels). The two different optical channel paths will be of different lengths, so as to avoid spectral overlap between the first and second beat frequencies.

For iNIRS systems of the present disclosure, a portion of the first optical channel path may share a common optical channel with a portion of the second optical channel path.

The common optical channel may couple either: (i) the light source to the object, or (ii) the object to the detector.

The plurality of optical channels may comprise: a sample delivery channel coupled to the light source and arranged to be coupled to the object for directing first and second sample light from the light source towards the object; a first sample receiving channel arranged to be coupled to the object for receiving first sample light therefrom; and a second sample receiving channel arranged to be coupled to the object for receiving second sample light therefrom. For example, the iNIRS system may have two separate sample receiving light channels. The first optical channel path may comprise (e.g. be provided by) the sample delivery channel and the first sample receiving channel. The second optical channel path may comprise (e.g. be provided by) the sample delivery channel and the second sample receiving channel. The first sample receiving channel may be of a different length to the second sample receiving channel, thereby to provide a difference in length between the first optical channel path and the second optical channel path. For example, the difference in optical channel path length may be provided using different length sample receiving channels. A reference channel may couple the light source to the detector. For example, the detector may be coupled to each of: (i) the first sample receiving channel for receiving first sample light, (ii) the second sample receiving channel for receiving second sample light, and (iii) the reference channel for receiving reference light.

The iNIRS system may comprise an analogue to digital converter, ADC, configured to obtain sample data containing an indication of the first and second beat frequencies detected by the optical detector. The sample data may comprise interferogram data. For example, the sample data may comprise data describing the interferogram obtained by the interferometer of the detector. That is, a first portion of the sample data may represent a portion of the interferogram which contains the first beat frequencies, and a second portion of the sample data may represent a portion of the interferogram which contains the second beat frequencies. The iNIRS system may be configured to use a single ADC channel to obtain the sample data for both the first and second beat frequencies. In other words, the ADC may be configured to obtain a digital signal representative of two simultaneously-obtained beat frequency distributions (first and second beat frequencies). That digital signal may be filtered and separated, e.g. using a FFT, to provide two separated distributions (that were obtained simultaneously using the same detector). The system may comprise a controller configured to process the sample data to obtain: (i) first sample data containing an indication of the first beat frequencies detected by the optical detector, and (ii) second sample data containing an indication of the second beat frequencies detected by the optical detector. For example, the controller may be able to separate data associated with the first sample light from data associated with the second sample light. Processing the sample data may comprise separating the first sample data from the second sample data based on an indication of beat frequency.

The controller may be configured to process the sample data so that: (i) the first sample data contains detected beat frequencies at below a threshold frequency, and (ii) the second sample data contains detected beat frequencies at above the threshold frequency. The controller may be configured to obtain: (i) first time of flight data for the first sample light based on the first sample data, and (ii) second time of flight data for the second sample light based on the second sample data. For example, the controller may first obtain time of flight data (e.g. for the interferogram) and then separate out the first and second sample data based on their respective times of flight. The controller may be configured to average the first time of flight data and the second time of flight data to provide combined time of flight data. The controller may be configured to align the first time of flight data with the second time of flight data based on a temporal offset associated with the difference in length between the first optical channel path and the second optical channel path (e.g. a difference in length between the first and second sample receiving and/or delivery channels). Aligning the first time of flight data with the second time of flight data may comprise at least one of: (i) applying a fixed temporal offset associated with the difference in duration of time taken for light to travel along the first and second optical channel paths (e.g. due to the difference in length of the sample receiving and/or delivery channels), and (ii) applying a temporal offset based on aligning one or more features in the first time of flight data with corresponding features in the second time of flight data. For example, the features may include a peak value (e.g. a time of flight at which a maximum intensity amplitude occurs), a minimum/maximum valve (e.g. a lowest or highest time of flight in the time of flight distribution), and/or an average value (e.g. an average, such as a mean, of all the registered time of flight values).

The difference in length between the first and second optical channel paths (e.g. between the first and second sample receiving and/or delivery channels) may be at least as large as a distance corresponding to an expected temporal width (e.g. a spectral width) for a distribution of time of flight, DTOF, associated with the first sample light. The iNIRS system may comprise a plurality of optical channels arranged to define three or more optical channel paths arranged to extend: (i) between the light source and the object, and (ii) between the object and the detector, and wherein each of the optical channel paths are of different lengths to each other to inhibit spectral overlap between beat frequencies associated therewith. For example, there may be three different sample receiving and/or delivery channels, each of different length to the others. The number of different optical channel paths (e.g. different combinations of sample delivery channels and sample receiving channels through which light may travel between the source and detector) may be selected based on a digitisation bandwidth for the single ADC channel. For example, the number (and arrangement) of different optical channel paths may be selected to maximise usage of the full digitisation bandwidth while inhibiting spectral overlap between the beat frequencies associated with each respective optical channel path.

The light detecting arrangement may comprise a beam combination element for combining light from the different sample receiving channels into a single channel. The detector may be coupled to said single channel for receiving sample light therefrom. The light source may be a first light source and the light emitting arrangement may comprise a second light source. The interferometric optical detector may be arranged to receive: first sample light from the second light source, second sample light from the second light source, and second reference light from the second light source.

The light detecting arrangement may be a first light detecting arrangement, and the iNIRS system may comprise a second light detecting arrangement, the second light detecting arrangement comprising a second detector. The plurality of optical channels may be arranged to define: a third optical channel path arranged to extend: (i) between the light source and the object for delivering third sample light from the light source to the object, and (ii) between the object and the second detector for delivering third sample light received from the object to the second detector; a fourth optical channel path arranged to extend: (i) between the light source and the object for delivering fourth sample light from the light source to the object, and (ii) between the object and the second detector for delivering fourth sample light received from the object to the second detector; and a second reference optical channel path arranged to extend between the light source and the second detector for delivering reference light from the light source to the second detector along a second reference channel. For example, the second light detecting arrangement may comprise: a third sample receiving channel arranged to be coupled to the object for receiving third sample light therefrom; a fourth sample receiving channel arranged to be coupled to the object for receiving fourth sample light therefrom (the third and fourth sample light each comprising light which was emitted from the light source); and the second interferometric optical detector may be coupled to: (i) the third sample receiving channel for receiving third sample light, (ii) the fourth sample receiving channel for receiving fourth sample light, and (iii) the reference channel for receiving reference light. The second detector may be arranged to combine: the reference light with the third sample light to provide light signals at a plurality of third beat frequencies between the third sample light and the reference light; and the reference light with the fourth sample light to provide light signals at a plurality of fourth beat frequencies between the fourth sample light and the reference light. The third optical channel path is of a different length to the fourth optical channel path to inhibit spectral overlap between the third and fourth beat frequencies (e.g. the third sample receiving channel may be a different length to the fourth sample receiving channel). The iNIRS system may be configured to average data obtained from each of the first to fourth detected beat frequencies (e.g. associated with each of the first to fourth sample light).

The plurality of optical channels may comprise: a first sample delivery channel coupled to the light source and arranged to be coupled to the object for directing first sample light from the light source towards the object; a second sample delivery channel coupled to the light source and arranged to be coupled to the object for directing second sample light from the light source towards the object; and a sample receiving channel arranged to be coupled to the object for receiving first and second sample light therefrom. The first optical channel path may comprise the first sample delivery channel and the sample receiving channel. The second optical channel path may comprise the second sample delivery channel and the sample receiving channel. The first sample delivery channel may be of a different length to the second sample delivery channel, thereby to provide a difference in length between the first optical channel path and the second optical channel path.

The plurality of optical channels may comprise: a first sample delivery channel coupled to the light source and arranged to be coupled to the object for directing light from the first light source towards the object; a second sample delivery channel coupled to the light source and arranged to be coupled to the object for directing light from the second light source towards the object; a first sample receiving channel arranged to be coupled to the object for receiving therefrom first sample light from the first sample delivery channel and first sample light from the second sample delivery channel; and a second sample receiving channel arranged to be coupled to the object for receiving therefrom second sample light from the first sample delivery channel and second sample light from the second sample delivery channel. The first sample delivery channel may be of a different length to the second sample delivery channel, and the first sample receiving channel may be of a different length to the second sample receiving channel to inhibit spectral overlap between each of: (i) first beat frequencies for first sample light from the first sample delivery channel, (ii) first beat frequencies for first sample light from the second sample delivery channel, (iii) second beat frequencies for second sample light from the first sample delivery channel, and (iv) second beat frequencies for second sample light from the second sample delivery channel.

Embodiments may provide an iNIRS system for neuro-imaging and analysis of a subject's brain tissue. For example, the object to be imaged may be a subject's brain. Where the image of the subjects brain is formed non-invasively by measuring many locations simultaneously. Many measurements are achieved with the combination of first and second source channels with the first and second receiving channels in a spatial pattern.

Each light source may comprise a light generating element arranged to generate light (e.g. near infrared light) and an optical arrangement for directing that light. For example, each light generating element may comprise a laser. The optical arrangement may be arranged to direct some of the light from the light generating element towards a region to be sampled. Each light delivery and/or receiving channel may comprise an optical channel, such as an optical fibre. Each optical channel may be configured for transmitting light along its length (e.g. from the light generating element towards the object to be imaged and/or from the object towards the light detector). The optical arrangement of each light source may comprise a light splitter for splitting light into each of the different delivery light channels. The iNIRS system may be arranged so that, when installed on a subject's head (e.g. for providing neuroimaging and analysis of that subject's brain tissue), the optical arrangement of each light source is configured to direct some of the light towards the subject's scalp (e.g. through one or more sample delivery channels). For example, the optical arrangement of each light source may comprise a light splitter configured to split light received from the light generating element into each of the different channels (e.g. onto the reference channel(s) and one or more sample delivery channels).

The iNIRS system may be arranged so that, in use when installed on a subject's head, the sample light may be directed towards the subject's scalp and brain tissue (e.g. through the sample delivery channel), and the reference light may be directed towards each light detector (e.g. through the reference delivery channel). Each light source may be arranged to provide (e.g. wavelength swept) emission of light (e.g. each light source may be arranged to output light at each of a plurality of different wavelengths in a selected time period). For example, each light source may comprise a modifying element for controlling operation of the light generating element to output light at each of a plurality of different wavelengths. Each light source may be arranged to sweep the wavelength of the light it outputs (e.g. increasing or decreasing in wavelength). Each light source may be arranged to provide chirped emission of light in which, each chirp (or 'pulse') comprises one wavelength sweep. Each light source may be arranged to output sequential chirps with the same wavelength sweep, e.g. such that the wavelength of the light output from the light source changes according to a repeating pattern.

Each light detector may provide an interferometric optical detector. Each light detector may comprise an optical arrangement. The optical arrangement of the light detector is configured to direct light to be detected into the light detector (e.g. from the subject's scalp). The optical arrangement of the light detector may comprise the one or more light receiving channels. The iNIRS system may be arranged so that, when installed on a subject's head (e.g. for providing neuroimaging and analysis of that subject's brain tissue), the optical arrangement of the light detector is configured to receive light emitted from the light source (e.g. which has travelled through the subject's brain tissue from the light source). The light detector may comprise a light combiner (e.g. for combining light on the reference receiving channel with light on the one or more sample receiving channels). Each light detector is configured to convert received combined light signals into one or more electrical signals indicative of that combined light signal (e.g. to provide interfero-gram data). For example, the detector may comprise one or more photodiodes. Each photodiode may output an electrical signal (e.g. a current) indicative of the combined light signal. The detector may comprise a balanced photodetector (e.g. which includes two photodiodes, which may be 180° out of phase with each other, and its output may be a combination of the two photodiode current outputs). The detector may optionally include current to voltage conversion circuitry and/or one or more amplifiers for amplifying the electrical signal. The amplifiers may be used with a specified gain to scale the voltage signal to achieve optimal dynamic range of the signals received from the brain (i.e. strong early arriving photons and late arriving photons.

The iNIRS system may include at least one analogue to digital converter arranged to convert electrical signals representing the sample light (e.g. the combined light signals) into one or more digital signals. The controller is arranged to process the digital signals to determine one or more properties of the subject's brain tissue. The controller may be configured to determine optical properties of the subject's brain tissue (e.g. for absorption and/or scattering). The controller may be configured to determine one or more dynamic properties of the subject's brain tissue (e.g. properties of the subject's brain tissue which are varying over time). For example, the controller may be configured to detect the presence of movement within the subject's brain tissue (e.g. due to movement, such as flow, of blood within the brain tissue).

The controller may be configured to process the digital signals to obtain time of flight information for photons of first and second sample light travelling from each light source through the subject's brain tissue to the light detector. The controller may be configured to identify penetration depths (and optionally expected trajectories for photons through the brain tissue) associated with the different times of flight for sample light photons. The controller may be configured to obtain a time-ordered series of time of flight distributions for sample light photons reaching each light detector.

The controller may be configured to process the time-ordered series to identify changes in the time of flight distribution over time, such as identifying decay and/or decay rates between success time of flight distributions. The controller may be configured to provide depth-resolved processing, e.g. by filtering the time of flight data to focus on only photons within a selected time of flight range (e.g. to identify changes in optical properties of the brain tissue for penetration depth(s) associated with that time of flight range). The controller may be configured to process data received from the light detector(s) to provide time of flight information with depth-resolved autocorrelations for the subject's brain tissue.

The controller may be configured to process the received data indicative of sample light received at a light detector and to output a control signal based on that received data. The control signal may provide an indication of the time of flight distribution (e.g. the controller may be configured to output the time of flight distribution). The control signal may provide an indication of one or more properties determined based on the time of flight distribution, such as optical properties for the brain tissue (e.g. scattering and/or absorption coefficients, and/or how these have changed/are changing). The control signal may provide an indication of blood flow within the subject's brain tissue. The control signal may provide a depth-resolved indication of one or more properties of the subject's brain tissue (e.g. linked to a specific region within their brain tissue, such as at a selected penetration depth range). The control signal may comprise an indication of one or more properties of the subject's brain tissue, such as intracranial pressure, blood flow index, artery elasticity, cerebral metabolic rate of oxygen consumption. The medical properties may be associated with specific regions/depths within the subject's brain tissue. The control signal may comprise an actuation command for a brain-computer interface, e.g. to control operation of a device based on the actuation command. The control signal may comprise an image for display, where that image represents a portion of the subject's brain tissue (as determined based on the received sample light).

FIGURES

Some examples of the present disclosure will now be described, by way of example only, with reference to the figures, in which.

In the drawings like reference numerals are used to indicate like elements.

SPECIFIC DESCRIPTION

The present disclosure relates to an iNIRS system for an object to be imaged. For this, the system is arranged for light to be directed towards the object along one or more sample delivery optical channels, and some of that light to be received from the object and directed towards an optical detector along one or more sample receiving optical channels. These optical channels are arranged so that there are at least two different optical paths between the source and the object and/or at least two different optical paths between the object and the detector. The channels are arranged for these optical paths to be of different lengths to each other. Light may therefore travel along a different length of optical channel when travelling from the light source to the detector (via the object to be imaged) depending on which of the channels that light travels through. This difference in optical channel length is of a sufficient length such that, when the received light is combined with reference light at the detector, there will be minimal, or no, spectral overlap between resulting beat frequencies associated with a first optical path length through the optical channels and a second optical path length through the optical channels. Two different time of flight distributions may therefore be obtained through one digitiser channel.

An example of an interferometric Near Infrared Spectroscopy ('INIRS') system will now be described with reference to FIG. 1.

Figure 1:
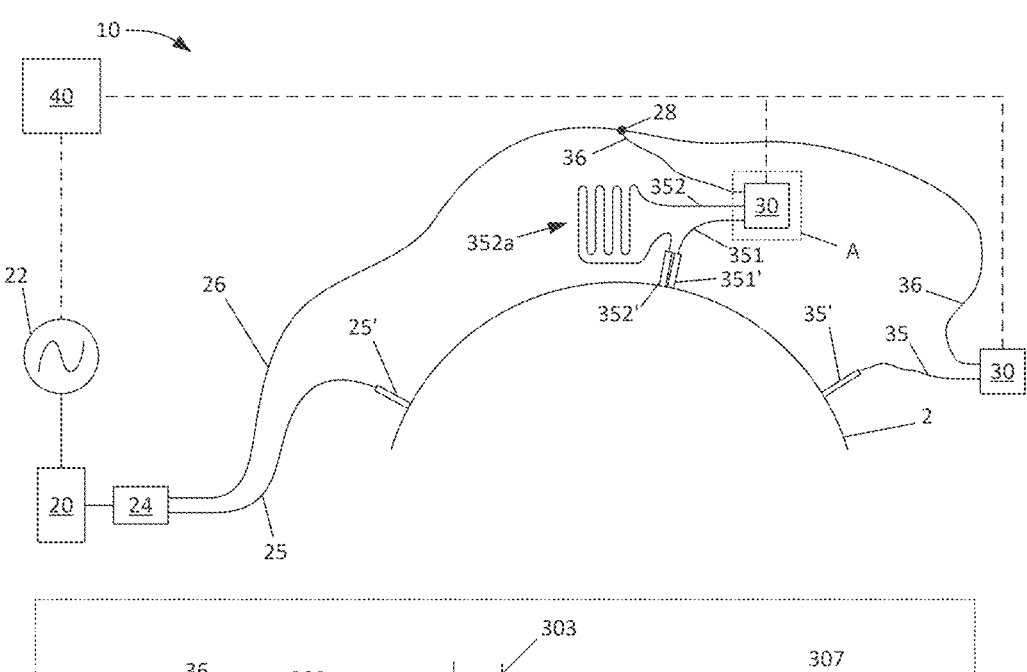
FIG. 1 shows a schematic diagram of an example iNIRS system.
Figure 1:
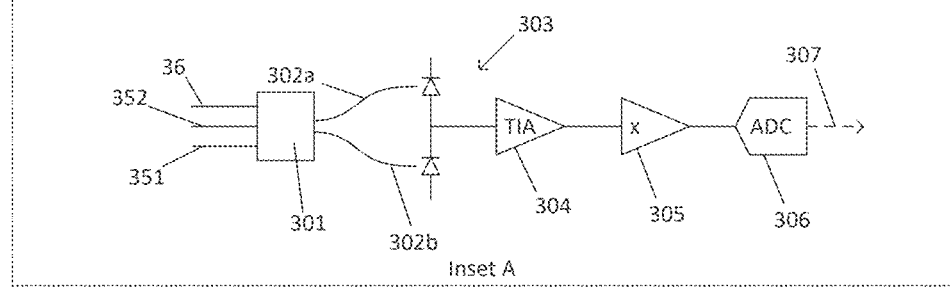

FIG. 1 shows a schematic diagram of an interferometric Near Infrared Spectroscopy ('INIRS') system 10. The iNIRS system 10 includes a light source 20, at least one detector 30, and a controller 40. The system 10 may include a plurality of detectors 30 although only two are shown in FIG. 1. Inset A shows a more detailed view of the light detector 30 shown in the dashed box listed A in FIG. 1.

The iNIRS system 10 may include a light source modifier 22, and a light splitter 24. The iNIRS system 10 includes a sample delivery channel 25 and a reference delivery channel 26. The iNIRS system 10 is shown coupled to an object to be imaged, which, in this example, may be a subject's head 2 (e.g. for providing neuroimaging). The iNIRS system 10 includes a sample delivery probe 25' and a plurality of sample receiving probes. In the example of the object being a subject's head 2, the probes may be for coupling optical channels to the subject's scalp.

Two light detectors 30 are shown in FIG. 1. Each light detector 30 has an associated reference receiving channel 36. The reference receiving channel 36 is for receiving reference light from the light source 20 (e.g. from the reference delivery channel 26. One of the light detectors 30 shown in FIG. 1 is coupled to the subject's scalp 2 via two optical channels: first sample receiving channel 351 and second receiving channel 352 (with first sample receiving probe 351' and second sample receiving probe 352' respectively). The other light detector 30 shown is coupled to the subject's scalp 2 via one optical channel: sample receiving channel 35 (with associated sample receiving probe 35'). As will be appreciated, a plurality of different sample receiving channels could be provided which are distributed about different regions of the subject's scalp (e.g. for imaging different regions of their brain tissue). Additionally, or alternatively, the sample receiving channels could be co-located on the subject's scalp, e.g. so that their obtained data may be averaged for the overlapping region each such channel is imaging. In other examples, the second sample receiving probe 35', sample receiving channel 35 and detector 30 need not be provided, and instead just the first probe/receiving channels/detector are provided.

The light source modifier 22 may comprise a source for providing a variable electrical control signal (e.g. a variable current or voltage provider). The light source modifier 22 is coupled to the light source 20. The light source modifier 22 may be electrically connected to the light source 20 to provide a variable current/voltage thereto.

The light source 20 may comprise a laser. For example, the laser may be a Distributed Feedback laser ('DFB') or a MEMS-Vertical Cavity Surface Emitting laser ('MEMS-VCSEL'). The light source 20 is coupled to the light splitter 24. The light splitter 24 has an input for receiving light from the light source 20. The light splitter 24 has two outputs for transmitting light from the light source 20 to two separate channels. The sample delivery channel 25 is coupled to the light splitter 24 (to receive light therefrom), as is the reference delivery channel 26. The sample delivery channel 25 couples the light splitter 24 to the sample delivery probe 25'. The sample delivery probe 25' will be placed at a location on the subject's scalp.

Other types of suitable laser include a Distributed Bragg Reflector laser ('DBR'), a Fourier Domain Mode Locking laser ('FDML'), a Vertical Cavity Surface-Emitting laser ('VCSEL'). Additionally, or alternatively, a pulsed super-continuum laser may be used in combination with a pulse stretching mechanism, such as a grating or GRISM pulse stretcher or length of dispersive optical fibre. For example, such an arrangement may be configured to temporally separate the wavelengths in the pulse such that a frequency chirped pulse is created (e.g. for ultimately providing an interferogram when sample and reference pulses are compared). Additionally, or alternatively, the wavelength sweeping may be provided by using a high coherence laser such as an external cavity diode laser (ECDL), DBR laser, feedback-stabilised laser or line-locked laser, and passing the output through an electro-optic IQ modulator. The IQ modulator may be driven by the electronic signal thereby to shift the wavelength of the light without needing to modulate the light source (e.g. laser) directly. This may result in higher coherence light than where the laser is directly modulated, which may provide an SNR benefit. This arrangement may also be combined with optical amplifiers to achieve a so-called Master Oscillator Power Amplifier (MOPA) configuration.

The reference delivery channel 26 couples the light splitter 24 to each of the light detectors 30. For each detector 30, a reference delivery connection 28 may be provided to couple the reference delivery channel 26 to the reference receiving channel 36 for that detector 30. Each reference receiving channel 36 is coupled to its light detector 30. In other words, each light detector 30 may be connected to the light source 20 to directly receive reference light therefrom (via one or more reference channels). Each sample receiving probe may be placed on the subject's scalp. Each sample receiving probe may be coupled to an associated sample receiving channel. Each sample receiving channel is coupled to its light detector 30. In other words, each light detector 30 is connected for indirectly receiving sample light from the light source 20 (e.g. to receive light which has travelled through a sample delivery channel, through a portion of the subject's head, and into a receiving channel associated with that detector 30).

There may be a plurality of different light detectors 30. Each detector 30 may provide an interferometer, such as a Mach-Zehnder interferometer (when receiving sample and reference light from the light source). Each of the different light detectors 30 may be coupled to the same light source 20 (each via one or more reference channels). The light detectors 30 may be spatially separated from the light source 20. The light detectors 30 may also be spatially separated from one another or they may be co-located on a sufficiently similar region of tissue that the received signals can be averaged together. For reference light to reach a light detector(s) 30 from the light source 20, the reference light will travel directly along one or more reference channels. For sample light to reach a light detector 30 from the light source 20, the sample light will travel indirectly via the subject's brain tissue. The sample light is directed towards the subject's scalp via one or more sample delivery channels 25'. The sample light may then pass through the subject's brain tissue and travel into a receiving channel and into the optical detector. The illumination of the subject's brain tissue may thus occur using a different light channel to the detection of light from the subject's brain tissue.

The controller 40 may comprise any suitable component with data receiving and processing functionality. For example, the controller 40 may include at least one Application Specific Integrated Circuit ('ASIC'). Other examples for the controller 40 may include a Field Programmable Gate Array ('FPGA') and/or a Data Acquisition module ('DAQ'). The controller 40 is coupled to each of the detectors. The controller 40 may be connected to each detector 30 via a wired connection (for receiving electrical signals indicative of detection therefrom), and/or the connection may be wireless (for receiving transmitted data indicative of detection therefrom). The controller 40 is coupled to the light source modifier 22. This connection may be wired or wireless.

The iNIRS system 10 may be at least partially housed within a garment for the subject's head 2. For example, the iNIRS system 10 may be provided in a hat/cap which is to be worn by the subject on their head 2. The head garment may be arranged to hold the light source 20 and detectors in a fixed arrangement relative to the subject's scalp. Some or all of the components may be provided with the head garment. For example, the head garment may include a plurality of receiving portions for receiving light source(s) 20 and light detectors 30. Channels connecting the light sources and light detectors 30 may be provided as part of the head garment (e.g. they may be routed through corresponding channel receiving portions of the head garment). The controller 40 may be separate to the head garment (e.g. and connected wirelessly) or it may also be provided as part of the head garment (e.g. by an ASIC within the head garment which may be wire coupled to the detectors and/or light source modifier 22). For example, the garment may be configured to receive the source and detection channels and the probes, with the other components of the system located elsewhere.

Some or all of the optical channels of the iNIRS system 10 may be provided by optical fibres. Light splitters of the present disclosure may comprise fibre-optic splitters. The iNIRS system 10 may include lenses, reflection and/or refraction devices for beam steering, as relevant. For example, the sample delivery probe 25' may include one or more lenses for spatially distributing sample light from the sample delivery channel 25 towards the subject's brain tissue. As another example, one or more of the sample receiving probes may include a lens for focusing received light into its associated sample receiving channel (as connected to that sample receiving probe). As another example, the probes may be bare fibres which have been cleaved and/or polished.

The iNIRS system 10 is arranged to provide a plurality of source-detector pairs for each light source 20. In other words, the iNIRS system 10 is arranged so that each light detector 30 may receive two forms of light: (i) reference light, and (ii) sample light. Each detector 30 is arranged to receive reference light directly from the light source 20 (the reference light will travel from the light source 20 along one or more channels to the light detector 30, e.g. without passing through the subject's brain tissue). Each detector 30 is also arranged to receive sample indirectly from the light source 20 (the sample light will have been directed towards the subject's scalp tissue and a portion may have travelled through their brain tissue en route to the detector 30, e.g. the sample light will not have travelled exclusively through optical channels between the light source 20 and light detector 30).

The detectors 30 are arranged to be positioned on the subject's scalp to provide imaging of a selected region of their brain. At least some of the detectors 30 are arranged to be spatially separated from the light source 20. One or more (e.g. each) of the light detectors 30 may be arranged to be sufficiently spaced apart from the light source 20 so that at least some of the photons of sample light from the light source 20 which is received at the light detector 30 will have penetrated into the subject's brain tissue. For example, the source-detector spacing may be selected so that the light detector 30 is arranged to receive sample light photons which have undergone multiple scattering events (e.g. which have scattered multiple times between source and detector as they travel through the subject's head 2). In other words, the source-detector spacings may be selected so that light detectors 30 are receiving deeply penetrating photons from the subject's brain tissue. Such photons may have longer times of flight from source to detector, as compared to photons which penetrate more shallowly and undergo fewer scattering events.

The detectors 30 may be arranged to be arranged to be spatially proximal to each other on the subject's scalp. The arrangement of the detectors 30 may be selected so that the detectors are imaging a similar region of the subject's brain. For example, the detectors 30 may be located within a threshold distance of each other on the subject's scalp so that the data they obtain may be averaged (e.g. to provide average values for the same volume of the subject's brain). That is, the detectors 30 may be arranged to spatially probe the same volume of tissue within the subject's brain. For example, the detectors may be arranged to be within one attenuation length for the tissue of each other (e.g. within the sum of the absorption and scattering coefficients).

The light source 20 is arranged to generate light and to direct this light towards the subject's scalp and the light detectors 30 (via the reference channel(s)). The light splitter 24 is arranged to receive light generated by the light source 20 and to split this light into two channels: (i) towards the subject's scalp using the sample delivery channel 25 and sample delivery probe 25', and (ii) to the light detectors 30 using the reference delivery channel 26 and reference receiving channels 36. The splitter is configured so that the majority of the light is directed towards the subject's scalp. For example, the splitter may be a 90:10 splitter, or a 99:1 splitter. The sample delivery channel 25 is arranged to receive sample light from the splitter, and to deliver this sample light towards the subject's scalp (via the sample delivery probe 25'). The reference delivery channel 26 is arranged to receive reference light from the splitter, and to deliver this sample light to the one or more detectors 30 (via the reference receiving channel(s) 36).

Each reference delivery connection 28 is arranged to deliver some of the reference light travelling along the reference delivery channel 26 to one of the reference receiving channels 36. Each of the reference receiving channels 36 is arranged to deliver the reference light to its light detector 30. The sample receiving probe is arranged to receive sample light from the subject's brain tissue. Each sample receiving probe may focus the received sample light onto its associated sample receiving channel. Each sample receiving channel may be arranged to deliver received sample light to its light detector 30. The sample receiving probes may be arranged in close proximity to each other on the subject's scalp.

For the iNIRS system of FIG. 1, the detector which is coupled to the subject's scalp via only one sample receiving channel 35 (and associated sample receiving probe 35') need not be provided. This detector is shown as an example to illustrate that multiple detectors may be coupled to the subject's scalp (and not all of the detectors need to be coupled to the subject's scalp via two or more sample receiving channels). However, for the following description, reference will predominantly be made to the detector 30 which is coupled to the subject's scalp via two or more sample receiving channels.

The detector 30 is coupled to the light source 20 via the reference receiving channel 36 (and reference delivery channel 26). The detector 30 is also coupled to the subject's scalp via two separate optical channels: the first sample receiving channel 351 and the second sample receiving channel 352. Each of these sample receiving channels may be coupled to the subject's scalp via a sample receiving probe (first and second sample receiving probes respectively). The first sample receiving channel 351 is of a different length to the second sample receiving channel 352. For this, the second sample receiving channel 352 includes additional optical channel length 352a (as shown in FIG. 1). In view of the additional optical channel length 352a, the distance light has to travel from the subject's scalp to the detector 30 through the second sample receiving channel 352 is less than the distance that light would have to travel through the first sample receiving channel 351.

The first sample receiving channel 351 may be coupled to the subject's scalp (e.g. via first sample receiving probe 351') at a location adjacent to the location at which the second sample receiving channel 352 is coupled to the subject's scalp. The first sample receiving channel 351 may therefore be arranged so that it is imaging a substantially similar (e.g. the same) region of the subject's brain to the second sample receiving channel 352. That is, on average, the light which enters the first sample receiving channel 351 and travels to the detector 30 is likely to be representative of the same region of the subject's brain as the light which enters the second sample receiving channel 352 and travels to the detector 30. The difference between the two being that the light which travels to the detector 30 via the second sample receiving channel 352 will travel a longer distance between the subject's scalp and the detector (due to the additional optical channel length 352a).

The detector 30 is arranged to receive three inputs: (i) reference light directly from the light source 20, (ii) sample light indirectly (e.g. which has travelled via the subject's brain tissue, as well as through their scalp skin and skull) from the light source 20 which has travelled via the first sample receiving channel 351, and (iii) sample light indirectly from the light source 20 which has travelled via the second sample receiving channel 352 along the longer optical path compared to the first sample receiving channel 351. For example, the detector 30 may comprise three or more input ports. A first input port of the detector 30 may be coupled to the reference delivery channel 26 for that detector 30. A second input port of the detector 30 may be coupled to the first sample receiving channel 351 for that detector 30. A third input port of the detector 30 may be coupled to the second sample receiving channel 352 for that detector 30. The detector is arranged to combine reference light with sample light (as an interferometer). The iNIRS system 10 (e.g. the detector 30 and the controller 40) may be arranged to determine one or more properties of the subject's brain tissue based on this combination of reference light and sample light (as will be described in more detail below). It will be appreciated in the context of the present disclosure that the combining of different light may be provided by a single component, or this may be staggered. For example, the first and second sample light may be combined into a single channel, and that single channel may then be combined with a reference light carrying channel, or three different channels may be combined into one channel with a single component.

From hereon in, sample light which is received at the detector 30 from the object to be imaged (e.g. the subject's brain), and which travelled along the first sample receiving channel 351 will be referred to as 'first sample light'. Similarly, sample light which is received at the detector 30 but which travelled along the second sample receiving channel 352 will be referred to as 'second sample light'. The second sample light will take a longer time to travel from the subject's scalp to the detector 30 than the first sample light due to the additional optical channel length 352a for the second sample receiving channel 352. Reference light is light which travelled directly through one or more optical channels (reference channels) to reach the detector 30 from the light source 20 (e.g. without passing through the object to be imaged).

The light source 20 is configured to provide wavelength swept emission of light. For this, the light source 20 may be configured to produce a series of emissions of pulses of light. During each pulse, the wavelength of light may be "swept" through a range of wavelengths. For example, the sweeping may be in the form of a chirped pulse. Light will be emitted at a plurality of different wavelengths during one pulse. For example, the wavelength may continually increase or decrease during one pulse (the rate of change of wavelength may be constant, or it may be variable). The series of chirped pulses may be contiguous (e.g. with a zero inter-pulse time interval). The light source 20 may be configured to successively emit a series of pulses, with each pulse having a wavelength sweep. However, it will be appreciated that the light source 20 need not provide continuous sweeping. For example, the light source could be tuned in steps rather than continuously, such that the light source 20 emits light at different wavelengths in different time intervals (e.g. discrete time intervals for emission at each of a plurality of wavelengths). The light source 20 may sweep unidirectionally (e.g. only increasing or decreasing in wavelength during one wavelength sweep), or it may sweep bidirectionally (e.g. both increasing and decreasing in wavelength during one wavelength sweep). Unidirectional sweeping can be beneficial as it increases the number of detected photons per sweep.

The controller 40 may be configured to selectively control the wavelength sweeping of the light source 20. The light source modifier 22 may be arranged to control the wavelength emission of light from the light source 20. For instance, the light source modifier 22 may be arranged to apply a selected current (or voltage) to the light source 20 to select a wavelength emission from the light source 20. The wavelength sweeping of the light source 20 may be controlled by using the light source modifier 22 to apply a corresponding electrical signal to the light source 20. The controller 40 may be arranged to control application of a current/voltage to the light source 20 using the light source modifier 22 to provide a selected pattern for the wavelengths of light emitted by the light source 20.

The light source 20 may be controlled to wavelength sweep according to a selected pattern for the sweeping. For example, the light source 20 may sweep through a selected range of wavelengths of light and/or the light source 20 may sweep through wavelengths of light according to a selected sweep profile (e.g. linear increasing, sinusoid, triangular etc.). For example, the light source 20 may sweep according to a selected sweeping rate, or a selected total sweeping time. The light source 20 is configured to wavelength sweep light so that during one wavelength sweep, light will be directed towards the subject's brain tissue through the sample delivery channel (and to the detectors via the reference channels) at each of a plurality of different wavelengths. The wavelength of light emitted by the light source 20 will vary over time. As such, an indication of the time at which light was emitted from the light source 20 may be determined based on a wavelength of that light.

The light source 20 may be configured to sweep through a selected wavelength range. For example, the light source 20 may be configured to sweep in optical frequency over a range of 50 GHz. For example, this may enable the light source 20 to emit modulated light at a plurality of different wavelengths between e.g. 829.94 nm and 830.06 nm when centred on 830 nm for example or between 1309.857 nm and 1310.143 nm when centred on 1310 nm for example. The light source 20 may be configured to sweep through a wavelength range of at least 0.025 nm, such as at least 0.05 nm, such as at least 0.075 nm, such as at least 0.1 nm, such as at least 0.11 nm (e.g. about a wavelength on which it is centred). The light source 20 may have a high output power, a long coherence time, and broad mode-hop free wavelength tuning. The light source 20 may have a relatively narrow linewidth and a longer coherence length, e.g. because the light source 20 will not sweep over particularly large bandwidths.

Light sources of the present disclosure may be configured to provide emission of high coherence light, e.g. substantially coherent light. It will be appreciated that the light source may not both emit perfectly coherent light and also provide wavelength swept emission of light, e.g. because light at different wavelengths will change phase at different rates. Light sources of the present disclosure may be controlled to sweep through a wavelength range which is relatively narrow compared to their absolute wavelength. In other words, the difference between the maximum and minimum wavelengths for one wavelength sweep will be relatively small compared to those wavelengths. Each light source may be configured to emit light (i.e. an electric field) which does not have much change in its phase over time.

The iNIRS system of the present disclosure will receive first sample light, second sample light, and reference light, all of which originated from the same light source (i.e. light source 20). The light sources of the present disclosure are configured to provide wavelength swept emission of sufficiently coherent light, such that sample and reference light, as received at the optical detector 30, will be in relatively similar (e.g. substantially similar) phase to each other. As such, combining sample light with reference light will give rise to substantially constructive interference between the two waves (e.g. a stream of sample light waves will have sufficiently similar phases to those of a corresponding stream of reference light waves so that the resulting combined light signal will contain a constructive combination of the two light waves). In other words, the coherence length of the light source may be such that the multiple scattering in the tissue will not reduce the coherence or fringe contrast below a noise floor for the measurement.

For example, each light source of the present disclosure may comprise a laser. The laser may be selected based on its coherence length, e.g. to enable the constructive interference described above between sample light and reference light to occur. In other words, the iNIRS system may be arranged so that a maximum expected time of flight delay for sample light photons (received at the optical detector which have travelled through the subject's brain tissue), e.g. which will be for the second sample light (as described in more detail below), relative to reference light photons (received at the optical detector which have travelled along the one or more reference channels) is within a coherence time period for the laser (e.g. the difference in optical path length between the sample and reference light is within the coherence length of the laser). Within this coherence time period, the phase of light emitted by the laser is approximately stable (despite changes in the wavelength of light being emitted). As such, there may be no loss in amplitude for combined light signals at the optical detector (e.g. the interference occurring at the detector may be substantially completely constructive).

For example, the iNIRS system may be configured to have a coherence length or range of approximately 50 m in air—e.g. the light sources may be selected which have a coherence length of between 50 and 100 m (a coherence time period of between 166 ns and 333 ns). It will be appreciated that this particular range is not intended to be limiting, rather it is illustrative of the approximate range for the light source. The light source may be selected so that it has a coherence length which is two or more times greater than the maximum expected optical path length difference, e.g. the coherence length may be three or four or more times greater. Having a light source with a coherence length which is much greater than the optical path length may increase accuracy for measuring sample light photons which have undergone a large number of scattering interactions within the subject's brain tissue.

The iNIRS system 10 is arranged so that the source-detector path lengths for reference and sample light are different. In other words, the iNIRS system 10 is arranged so that an average, or expected, optical path length for light travelling from the light source 20 to each detector via the subject's brain tissue will be different to the optical path length for light travelling from the light source 20 to said detector via reference channel(s).

The iNIRS system 10 is arranged so that sample light may travel along two or more different paths of optical channels when travelling from the source 20 to the detector 30. As such, sample light may be able to travel along different paths through the optical channels (in addition to travelling through different paths through the subject's head). The iNIRS system 10 includes at least two different routes of optical channels through which sample light could travel to the detector 30 from the light source 20 (in addition to travelling through the subject's brain). In the example shown in FIG. 1, the different optical channel paths are those extending from the object to be imaged (e.g. the subject's scalp) to the detector 30. That is, sample light may be directed towards the object from the light source 20 (along sample delivery channel 25) and that sample light may travel through the object and to the detector 30, where the route from the object to the detector 30 is either along the first sample receiving channel 351 or the second sample receiving channel 352. In other words, the iNIRS system 10 is arranged to provide two or more different source-detector optical path lengths for sample light (irrespective of whichever route that sample light takes when travelling through the object to be imaged).

As will be appreciated in the context of the present disclosure, photons of sample light which are directed towards the subject's brain tissue may travel from the light source 20 to a light detector 30 via a practically infinite number of different paths. A photon of sample light may undergo a large number of scattering events, and so follow a very tortuous path, between the sample delivery probe 25' and the sample receiving probe 35'. The iNIRS system 10 may be arranged to provide neuroimaging and analysis based at least in part on activity in the subject's brain tissue. The time of flight for a sample light photon from light source 20 to light detector 30 will of course increase as the path length it takes increases. As such, a photon which travels a longer path, and penetrates deeper into the subject's brain tissue, will take even longer to arrive at the light detector 30. The longer the time of flight for a sample light photon, the deeper that photon is likely to have penetrated into the subject's brain tissue.

The iNIRS system 10 may be arranged so that the shortest time of flight for photons of light to travel from light source 20 to light detector 30 will be for photons of reference light travelling along the reference channel(s). Sample light photons will have longer times of flight than this reference light. The sample light photons which penetrate deeper into the subject's brain tissue are likely to be those which have a longer time of flight to the light detector 30. The additional optical path length 352a is arranged such that the difference in optical path length between the first sample receiving channel 351 and the second sample receiving channel 352 means that first sample light photons will have shorter times of flight than second sample light photons.

As will be appreciated in the context of the present disclosure, the path which each individual sample light photon travels through the object to be imaged (between sample delivery channel and sample receiving channel) cannot be predicted. However, where there are a great number of these sample light photons, the overall time of flight distribution for such sample light photons may be modelled statistically. As such, for a given source-detector pair, one or more expected properties for a time of flight distribution for sample light may be known. For instance, for each source-detector pair, an expected time difference between the shortest time of flight photons and the longest time of flight photons (e.g. a spectral width) may be known. For example, this may be based on previous observable signals for the earliest arriving detectable photons and the latest arriving detectable photons. In other words, for any given source-detector pair, there may be a known maximum expected spectral width for a resulting time of flight distribution for sample light photons.

In other words, photons of the first and second sample light will each provide a photon distribution spanning from an earliest arriving sample light photon to a latest arriving sample light photon. Before the earliest photon and after the latest photon, no incident photons can be resolved above a noise floor of the system. This difference in time between first and last detected incident photons (and thus difference in frequency between the associated lowest and highest beat frequency) provides a width or range for the distribution of incident photons. The additional channel length may be selected based on this temporal width/range for the sample light photons from the first and second light. For example, this may be selected based on a D4σ width (e.g. as per the beam diameter determination ISO 11146).

The iNIRS system 10 may effectively provide two source-detector pairings between the same source 20 and detector 30. In the example of FIG. 1, this is due to the two different optical paths that are provided between the object and the detector 30 (e.g. due to the first and second sample receiving channels 351, 352). There will be a known expected spectral width for the time of flight distribution for the first sample light photons (e.g. a known time interval spanning between the shortest and longest times of flight for first sample light photons). For example, this spectral width may be somewhere in the region of 0.5 to 2 ns. The additional optical channel length 352a may add an additional distance of optical channel along which second sample light photons have to travel to reach the detector 30, where that additional distance corresponds to at least the expected spectral width for the first sample light photons. For example, the additional optical channel length 352a may have a distance which is at least as long a distance corresponding to a combination of both: (i) the expected spectral width for the first sample light, and (ii) an additional buffer time period (selected so that anomalously long first sample light photon times of flight are still reaching the detector before any of the second sample light photons).

In other words, the additional optical channel length 352a adds an additional distance of optical channel of such a length that the duration of time it takes for second sample light photons to travel along that additional length of optical channel will be at least as long as the expected spectral width of the first sample light photon time of flight distribution. The additional optical channel length 352a is arranged so that detectable photons of first sample light may always have shorter times of flight than detectable photons of second sample light. For example, the photons of first sample light with the longest times of flight through the object to be imaged and that are detected by the detector 30 will still have shorter overall times of flight from source 20 to detector 30 than the photons of second sample light which have the shortest times of flight through the object to be imaged.

The iNIRS system 10 is arranged so that the detector 30 is configured to receive three inputs: reference light (from the reference receiving channel 36), first sample light (from the first sample receiving channel 351) and second sample light (from the second sample receiving channel 352). The detector 30 is configured to combine the three using a light combiner. For example, the detector may provide an interferometer assembly (in combination with the first and second sample channels and the reference channel) configured to combine reference and sample light to obtain an interference pattern (an interferogram). The obtained interference pattern may comprise a contribution associated with the first sample light (and first sample receiving channel 351) and a contribution associated with the second sample light (and second sample receiving channel 352).

The light source 20 is configured to emit substantially coherent light. The resulting interference pattern for light from the light source 20 (as obtained at each detector) may comprise a combined signal having components that beat (or intermediate/difference) frequencies corresponding to the difference in wavelength between: (i) wavelengths of photons of sample light received at the light detector 30 at a given instance in time, and (ii) the wavelength of photons of reference light received at the light detector 30 at that instance in time. The reference light at a single sampling interval should be substantially narrow and uniform wavelength as limited by either the intrinsic linewidth of the laser and the optical frequency sweeping rate, as the received photons of reference light will have travelled the same distance (through reference channels) to the light detector 30 from the light source 20.

The sample light received at the detector 30 (to be combined with reference light) will include photons of first sample light and photons of second sample light. These received photons will be at different wavelengths. Photons of first sample light received at the detector 30 will have taken different, unique, paths through the object to be imaged. As such, these photons of first sample light received at the detector 30 will have different times of flight to each other, and thus they will be at different wavelengths to each other (due to the wavelength swept emission from the light source 20). Similarly, the photons of second sample light received at the detector 30 will have had different times of flight through the object, and thus these photons will be at different wavelengths to each other.

The additional optical path length 352a is arranged so that the photons of first sample light received at the detector 30 will contain photons in a first wavelength range, and the photons of second sample light received at the detector 30 will contain photons in a second wavelength range. The additional optical path length 352a may have a length selected so that there is no overlap between the first wavelength range and the second wavelength range.

The resulting interferogram obtained by the detector 30 will therefore contain a plurality of different beat frequencies (due to the different differences in wavelength). The detected second sample light will be at higher beat frequencies than the detected first sample light (as the photons of second sample light will have had longer times of flight). Within the range of beat frequencies obtained for each of the first and second sample light, the higher beat frequencies may correspond to photons with longer times of flight (e.g. deeper penetrating photons). It is to be appreciated that, in this example, the reference light will travel a shorter distance to reach the detector than the sample light. Of course, the alternative could be provided in which the sample light travels less far than the reference light—in which case, the higher beat frequencies will be associated with the shortest times of flight. However, in this example, the reference light will be assumed to be travelling less far than the sample light.

The iNIRS system 10 may be configured to obtain a digital representation of each resulting interferogram. For example, the detector 30 may include an analogue to digital converter ('ADC') configured to obtain interferogram data from each interferogram provided by the detector 30. One example of circuitry for obtaining such interferogram data will be described below in relation to Inset A of FIG. 1. Each obtained interferogram may be Fourier analysed (e.g. using an FFT or IFT) for obtaining an indication of a distribution of time of flight ('DTOF') for sample light photons incident on the light detector 30. Each determined DTOF may provide a distribution showing the time of flight for all sample light photons which were incident on the light detector 30 at a given moment in time. The DTOF may contain an ensemble average representing a large number of incident photons (in each of a plurality of different time of flight, 'TOF', bins). The intensity for each TOF bin will provide an indication of the number of incident photons in that TOF bin (e.g. for all incident photons having a time of flight within a range of time of flights covered by that TOF bin). A phase of a TOF bin (e.g. obtained using a Fourier analysis) may represent an average phase for all of the photons arriving in that TOF bin.

In the example of FIG. 1, the detector 30 will obtain an interferogram which effectively contains two separate DTOFs: one for photons of first sample light which have travelled through the object to be imaged, and one for photons of second sample light which have travelled through the object to be imaged. An example of such obtained interferogram data is shown in FIG. 2.

Figure 2:
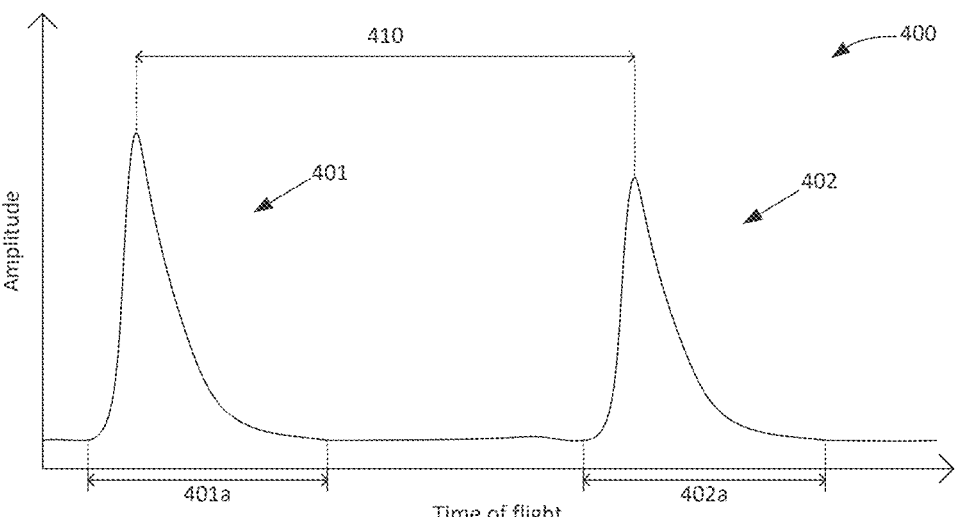
FIG. 2 shows a graph depicting time of flight data for incident photons.

FIG. 2 shows a plot 400 of amplitude versus time of flight for photons of sample light received at the detector 30. The data shown in FIG. 2 may have been obtained by performing an FFT on obtained interferogram data. The amplitude may provide an indication of the total number of photons detected at each time of flight. The plot 400 includes: first sample light data 401 containing photons of first sample light received in a first time of flight range 401a, and second sample light data 402 containing photons of second sample light received in a second time of flight range 402*a*. The data shown in FIG. 2 may have been obtained using a single digitiser channel of the ADC. As can be seen in FIG. 2, the first sample light data 401 is contained in a much lower time of flight range than the second sample light data 402. The plot 400 effectively contains two separable DTOFs: one for the first sample light and one for the second sample light.

Each DTOF follows a similar distribution. This distribution includes an initial sharp peak followed by a gradually diminishing tail. The ends of the DTOF may be defined by the points at which any signal associated with that DTOF is no longer distinguishable from background noise. In other words, the points at which a DTOF starts and ends for detected sample light are the points where the number of received sample light photons are sufficiently small (or non-existent) that a detected amplitude at those beat frequencies (i.e. times of flight) is not significantly (e.g. statistical significance) greater than a detected amplitude associated solely with background noise (rather than incident sample light photons). That is, the detected amplitude at those beat frequencies is not consistently above a noise floor for the system (e.g. with an average of less than one incident photon at that frequency per measurement).

The two DTOFs shown in the plot 400 of FIG. 2 are separated from each other by a separation time 410. The separation time 410 is a temporal offset between the first DTOF (for first sample light) and the second DTOF (for second sample light) that are contained within the data. In FIG. 2, this separation time 410 is shown as a temporal offset between the peak value of the first sample light data 401 and the peak value of the second sample light data 402. However, it is to be appreciated that the separation time 410 may be a temporal offset between other suitable points in each time of flight distribution, such as between the lowest time of flight for first and second sample light, the longest time of flight for first and second sample light, and/or an average value for first and second sample light time of flights (e.g. a mean time of flight for first and second sample light). In other words, the separation time 410 represents a difference in detected times of flight for the first and second sample light photons.

The separation time 410 corresponds to the additional optical channel length 352*a* associated with the second sample light received at the detector 30. The separation time 410 is longer than a spectral width for the first sample light data 401 (e.g. the separation time 410 is greater than the amount of time separating the start and end of the first time of flight range 401*a*). As can be seen in FIG. 2, there is no spectral overlap between the first sample light data 401 and the second sample light data 402. The first sample light data 401 may be separable from the second sample light data 402. In other words, two separate DTOFs may extracted from the obtained interferogram (one for first sample light and one for second sample light). Each of these separate, extractable, DTOFs may not contain any time of flight data which corresponds to photons from the other sample light.

The controller 40 of the iNIRS system 10 may be configured to process the interferogram data. The controller 40 may be configured to process the interferogram data obtained from the detector 30 (and ADC) to obtain DTOF data for the first sample light and DTOF data for the second sample light. As set out above, this DTOF data may be indicative of beat frequency data. That is, the first DTOF data may correspond to first beat frequency data, and the second DTOF data may correspond to second beat frequency data. The controller 40 may be configured to extract first DTOF data and second DTOF data. This may comprise separating out the two DTOFs contained in the interferogram. The controller 40 may be configured to separate based on an indication of time of flight. The indication of time of flight may comprise an indication of a value for the beat frequency (e.g. prior to processing this data to obtain DTOF data), or an indication of time of flight (e.g. as obtained from the processed DTOF data).

The controller 40 may be configured to process the interferogram data to obtain two different DTOFS. The controller 40 may be configured to perform imaging for the object (e.g. neuroimaging of a subject's brain) based on both of the two different DTOFs obtained from the same interferogram data. The controller 40 may be configured to first separate out the two different DTOFs from the interferogram data. This may comprise identifying the first DTOF data as all data points below a first threshold time of flight (and optionally above a lower threshold time of flight, which is less than the first threshold time of flight), as well as identifying the first DTOF data as all data points above a second threshold time of flight (and optionally below an upper threshold time of flight, which is more than the second threshold time of flight). The first and second threshold time of flight may be the same time, or they may be different (with the second threshold time of flight being greater than the first time of flight).

In other words, the controller 40 may be configured to obtain: (i) first DTOF data containing a distribution of time of flight values for first sample light, and (ii) second DTOF data containing a distribution of time of flight values for second sample light. The time of flight values derived from the interferogram data may indicate that the times of flight for the first sample light are lower than those for the second sample light. However, as will be appreciated, this difference in time of flight value is at least in part brought about due to the additional optical channel length 352*a* through which the second sample light has to travel compared to the first sample light.

The controller 40 may be configured to compensate for this apparent difference in times of flight between the first and second sample light. For this, the controller 40 may be configured to align the first DTOF (for the first sample light) with the second DTOF (for the second sample light). The iNIRS system 10 is configured to provide imaging of an object to be imaged based on time of flight data associated with the times of flight for photons, and how these times of flight change, for the travelling of photons through the object to be imaged (e.g. through a subject's brain). As such, the controller 40 may be configured to process the obtained DTOF data to obtain data which describes the different times of flight for photons travelling through the object (e.g. between the point at which sample light leaves the sample delivery channel 25 and the point at which the sample light enters the first/second sample receiving channel 351, 352).

The controller 40 may be configured to align the first DTOF data with the second DTOF data. For example, the controller 40 may apply a temporal offset to one or both of the first and second DTOF data. The temporal offset may be selected so as to remove the influence of the additional optical channel length 352*a* on the time of flight data for the second DTOF. For example, the controller 40 may align the first and second DTOF so that they both only contain information about photon time of flight through the object (rather than also through channel(s) between light source and object, and/or through channel(s) between object and detector). The controller 40 may be configured to align the first and second DTOF by applying a fixed temporal offset associated with the difference in duration of time taken for light to travel along the first and second sample receiving channels. The controller 40 may be configured to align the first and second DTOF by applying a temporal offset based on aligning one or more features in the first time of flight data with corresponding features in the second time of flight data, such as by aligning based on a peak TOF value, an average TOF value, and/or a maximum or minimum TOF value for each of the two DTOFs.

As such, the controller 40 of the iNIRS system 10 may be configured to obtain two pieces of DTOF data (e.g. first and second DTOF data) using one light source 20 and one light detector 30. The controller 40 may obtain these two pieces of DTOF data using only one ADC, e.g. which digitised both DTOF distributions simultaneously within the same interferogram obtained by the detector 30. The iNIRS system 10 may therefore be configured to obtain twice as much data for each such source-detector pair. The first and second sample receiving channels 351, 352 may be arranged proximal to each other on the object to be imaged. The controller 40 may be configured to average the first and second DTOF data for the object. For example, the iNIRS system 10 may be configured to sequentially obtain a series of interferograms (and thus interferogram data). For each item of interferogram data, the controller 40 may be configured to obtain first and second DTOF data. The controller 40 may be configured to provide imaging of the object (e.g. neuroimaging of a subject's brain) based on a temporal evolution of the DTOF data (e.g. based on how the time of flight distributions evolve over time). For this, the first and second DTOF data in each item of interferogram data may be combined to provide averaged DTOF data, and the imaging of the object may be based on temporal evolution of sequential items of averaged DTOF data.

One example of an arrangement for converting received light signals into digital data is shown in Inset A of FIG. 1. Inset A shows an arrangement of components that may be used as part of a light detector 30 of the present disclosure. As shown in the iNIRS system 10 of FIG. 1, the detector 30 is arranged to receive three inputs: (i) reference light which has travelled along reference delivery channel 26 and reference receiving channel 36, (ii) first sample light which has been received through the first sample receiving channel 351, and (iii) second sample light which has been received through the second sample receiving channel 352.

As shown, the detector may include a light combiner and splitter 301, a first light channel 302a and a second light channel 302b, a balanced photodetector 303, a transimpedance amplifier 304, an amplifier 305, an analogue to digital converter ('ADC') 306. The ADC 306 is arranged to provide a digital signal output 307.

The light combiner and splitter 301 is coupled to both the reference receiving channel 36, the first sample receiving channel 351 and the second sample receiving channel 352. The light combiner and splitter 301 is arranged to receive the first sample light, the second sample light and the reference light, and to combine these to provide a combined light signal. For example, the first and second sample receiving channels 351, 352 may combined into a beam combination element. This combination could be achieved using e.g. fused fibre couplers, polarisation combiners, beam splitter cubes, diffraction gratings or more other splitting/combining optical elements such as Photonic Lanterns and fibre to free-space to fibre multiplexing optics.

Each sample receiving channel may comprise a single-mode fibre ('SMF') or a few-mode fibre ('FMF'). Each sample receiving channel may be coupled to an additional fibre in the form of a multi-mode fibre ('MMF') or an FMF.

Each sample receiving channel may be coupled to that additional fibre and arranged so that each sample receiving channel (e.g. each SMF or FMF) excites its own unique mode within the additional fibre. The reference channel(s) may be provided by an SMF or a FMF (typically an SMF). The reference channel may be coupled to the additional fibre, e.g. to excite a fundamental mode of the additional fibre. The additional fibre may be the arranged to combine the light in a FMF or MMF fibre coupler. Alternatively, sample light in a FMF/MMF could be combined with the reference light using one or more free-space beam combining elements such as a beamsplitter cube.

The light combiner and splitter 301 may be arranged to split the resulting combined light signal onto two separate channels: the first light channel 302a and the second light channel 302b. For example, this may be a 50:50 split (or there or thereabouts). The first light channel 302a and second light channel 302b may be coupled to a balanced photodetector 303. Each light channel may be arranged to direct light towards an associated photodiode. The balanced detector may be arranged to provide an output based on a difference between outputs from the two photodetectors. The two photodetectors will typically be provided so that the beat signals on each photodiode are 180° out of phase with each other, and so the coherent AC terms will combine positively with each other. The balanced photodetector 303 may be arranged to output a current corresponding to the difference between the two photodetector output currents. The balanced photodetector 303 may remove any unwanted DC terms from this signal, such as slow fluctuations emanating from the light source 20 or other common-mode effects such as noise.

The light detector 30 may be configured to use a current to voltage converter to convert the current output from the balanced photodetector 303 into a corresponding voltage. As shown in Inset A of FIG. 1, the converter may comprise a transimpedance amplifier 304. The voltage output from the transimpedance amplifier 304 may then be amplified using the amplifier 305. The amplifier may be used to scale the output signal to the full range of the ADC and limit the electronic frequency of the circuit to further maximise the SNR. This amplified voltage is then provided to the ADC 306 to be digitised. The ADC 306 comprises a digitiser having sufficient bandwidth so that the full signal bandwidth containing time of flight information may be digitised without attenuation. As will be appreciated in the context of the present disclosure, and as described in more detail below, the ADC may have a digitisation bandwidth which is far greater than that of a single DTOF. By effectively providing more DTOFs in each interferogram to be digitised, the iNIRS system 10 may utilise a greater proportion of the digitisation bandwidth for each ADC 306 of the system 10.

For example, the digitiser bandwidth may be at least as large as the bandwidth for the combined light signal (e.g. the digitiser bandwidth may be sufficiently large to process a plurality of different DTOF distributions included in one interferogram). For example, the digitiser may be selected to have a sampling rate high enough so that the Nyquist criterion is met for the bandwidth of the signal to be processed. The digitiser may be provided as part of each light detector 30, or the digitiser may be part of the controller 40, and the controller 40 may be coupled to each of the light detectors 30 to receive electrical signals therefrom which are to be digitised. For each combined light signal, a digital signal output 307 will be provided which gives a digital representation of that combined light signal (and thus of the sample light incident on the light detector 30 at the moment in time when that combined light signal was generated and measured).

The iNIRS system 10 is configured to obtain a plurality of digital signal outputs 307 indicative of sample light incident on light detectors 30. In particular, each light detector 30 is configured to repeatedly combine light signals (first sample, second sample and reference) for providing digital signal outputs 307 representative of each combined light signal. For example, for each light detector 30, a time series of digital signal outputs 307 may be obtained, wherein each subsequent digital signal output 307 is for a subsequent point in time at which a combined light signal was obtained and measured (and the digital signal output 307 represents that combined light signal as obtained and measured). As described above, each digital signal output 307 may be in the form of interferogram data indicative of an interferogram obtained using the detector 30 (from which two or more sample light DTOFs may be obtained for that point in time at that detector 30).

In the examples described herein, the iNIRS system 10 is configured to obtain interferogram data which effectively contains an indication of two separate DTOFs (one for the first sample light and one for the second sample light). In the example of FIG. 1, two sample receiving channels are provided, with a delay in one of those sample receiving channels, so that one source 20 and one detector 30 may be used for obtaining two separate DTOFs. However, it will be appreciated in the context of the present disclosure that similar functionality may be provided by introducing a delay into one of two or more sample delivery channels (in addition to, or as an alternative to, introducing a delay into one of two or more sample receiving channels). An example of such an arrangement will now be described with reference to FIG. 3a.

Figure 3A:
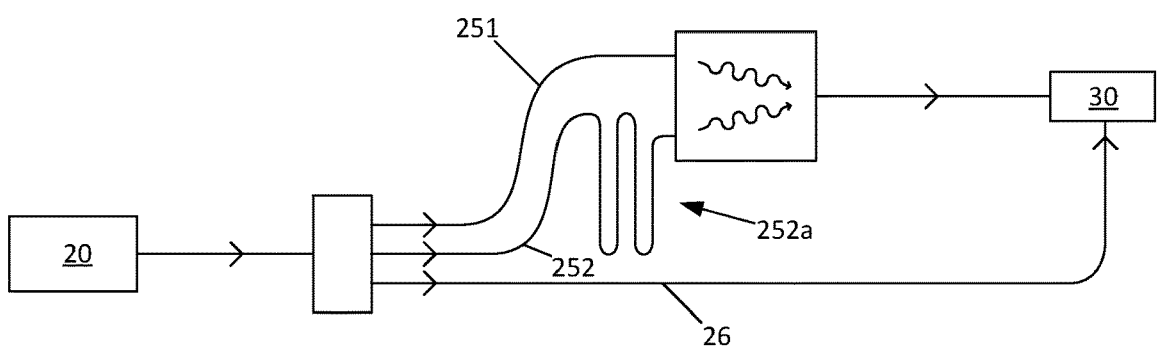
FIGS. 3a to 3e show schematic diagrams of example iNIRS systems.

FIG. 3a shows an iNIRS system. As with the system of FIG. 1, there is a light source 20, a detector 30, and an object to be imaged. However, in FIG. 3a, there is a first sample delivery channel 251 and a second sample delivery channel 252. Each sample delivery channel 251, 252 couples the light source 20 to the object to be imaged. The iNIRS system also includes a sample receiving channel and a reference channel 26 (only one of each are shown in FIG. 3a). The detector 30 is arranged to combine reference light carried on the reference channel 26 with sample light carried on the sample receiving channel.

In FIG. 3a, an additional optical channel length 252a is provided in the second sample delivery channel 252. The additional optical channel length 252a shown in FIG. 3a is arranged to provide the same functionality as the additional optical channel length 352a shown in FIG. 1. That is, the additional optical channel length 252a is arranged so that some of the sample light incident at the detector will have a substantially longer time of flight as compared to other sample light incident at the detector (where that additional time of flight is due to the sample light travelling along an additional length of optical channel). In FIG. 3a, the light source 20 is configured to direct first sample light towards the object through the first sample channel 251 and second sample light towards the object through the second sample channel 252. Both the first and second sample light may be received at the same sample receiving channel. Each of the first and second sample light may then be combined with reference light to provide first and second beat frequencies. As with the example of FIG. 1, the additional optical channel length 252a is selected to inhibit spectral overlap between beat frequencies associated with the first sample light and beat frequencies associated with the second sample light. The light source 20 may be coupled to a light splitter which is configured to split light from the light source 20 between: (i) first sample light to be directed towards the object along the first sample delivery channel 251, (ii) second sample light to be directed towards the object along the second sample delivery channel 252 (and through the additional optical channel length 252a), and (iii) reference light to be directed towards the detector 30 along one or more reference channels.

Another example iNIRS system will now be described with reference to FIG. 3b. One advantage with the system of FIG. 1 (as compared to that of FIG. 3a) is that, if more light sources are added to the system, these light sources may combine with the existing two sample receiving channels so that first and second sample light may be provided to the detector 30 for each light source (where the second sample light has an optical delay as compared to the first sample light). Alternatively, as in the case of FIG. 3a, where multiple different detectors are added, each detector may have only one sample receiving channel, but that detector may be receiving first and second sample light from the light source.

Figure 3B:
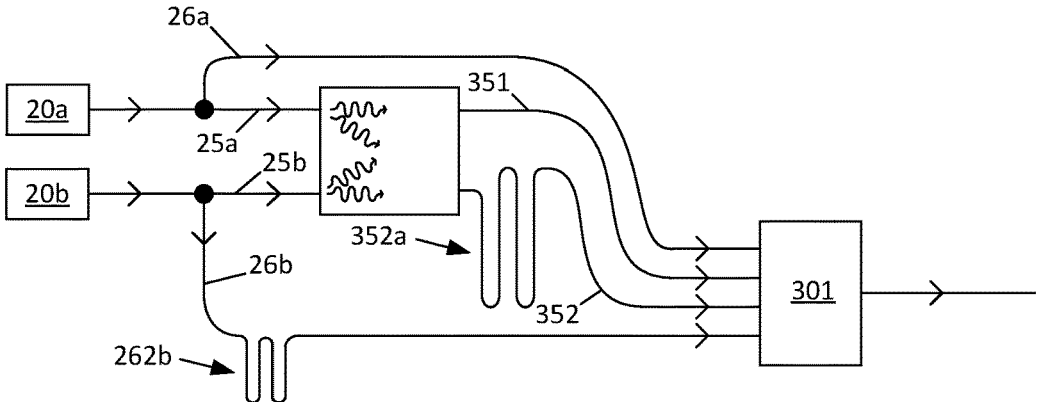

FIG. 3b shows an iNIRS system which includes a first light source 20a and a second light source 20b. The first light source 20a is coupled to: (i) the object via a sample delivery channel 25a, and (ii) the detector (e.g. light combiner 301 of the detector) via a reference channel 26a. The second light source 20b is coupled to: (i) the object via a sample delivery channel 25b, and (ii) the detector (e.g. light combiner 301) via a reference channel 26b. The system includes first and second sample receiving channels 351, 352 of the type described above in relation to FIG. 1 (e.g. with an additional optical channel length 352a in the second optical channel 352). The iNIRS system may be arranged so that the first sample receiving channel 251 may receive first sample light from the first light source 20a and first sample light from the second light source 20b, and the second sample receiving channel 252 may receive second sample light from the first light source 20a and second sample light from the second light source 20b.

The system may be arranged to inhibit spectral overlap between the four different received light signals. For example, one of the reference channels 26a, 26b may have an additional optical channel length designed to introduce a time of flight delay into that reference channel. In FIG. 3b, this is shown by a reference additional channel length 262b in the second reference channel 26b. This additional optical channel length 262b for the reference channel (second reference channel 26b), and the additional optical channel length 352a for the second sample receiving channel 352 may be selected so that all four beat frequency distributions may fit on the same interferogram without spectral overlap. Additionally or alternatively, the system may be configured to provide temporal multiplexing of the operation of the two light sources so that only one light source is operated at a time (and thus the additional optical channel length 352 may itself inhibit spectral overlap between in the interferogram, e.g. without the need for reference additional channel length 262b).

Figure 3C:
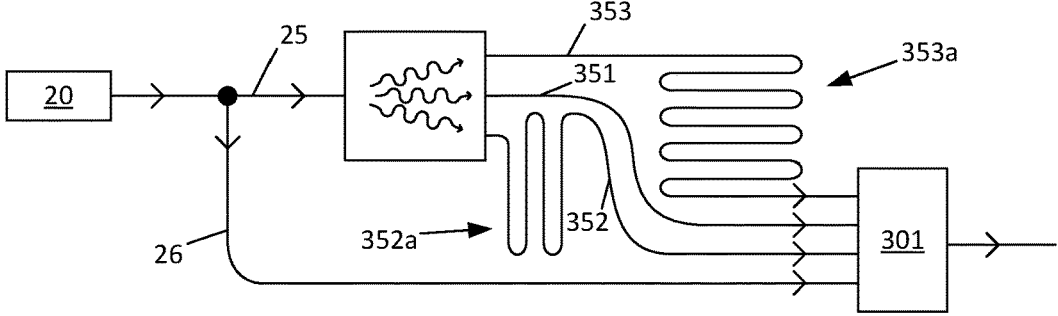

FIG. 3c shows another example iNIRS system. In the iNIRS system of FIG. 3c, there is one light source 20 and one detector (although only the light combiner 301 of the detector is shown). The light source 20 is coupled to the object via a sample delivery channel 25, and to the detector (combiner 301) via a reference channel 26. The system of FIG. 3c is similar to that of FIG. 1, except that the system of FIG. 3c includes a third sample receiving channel 353. The third sample receiving channel 353 includes an additional optical channel length 353a, which is of a different length to the additional optical channel length 352a of the second optical channel 352. The three sample receiving channels are arranged to be of different lengths so that three separate beat frequency distributions may be contained within one interferogram without spectral overlap. For example one of the additional optical channel lengths 352a, 353a may be significantly bigger than the other to provide a further increase in time of flight to sample light photons travelling along that channel.

Figure 3D:
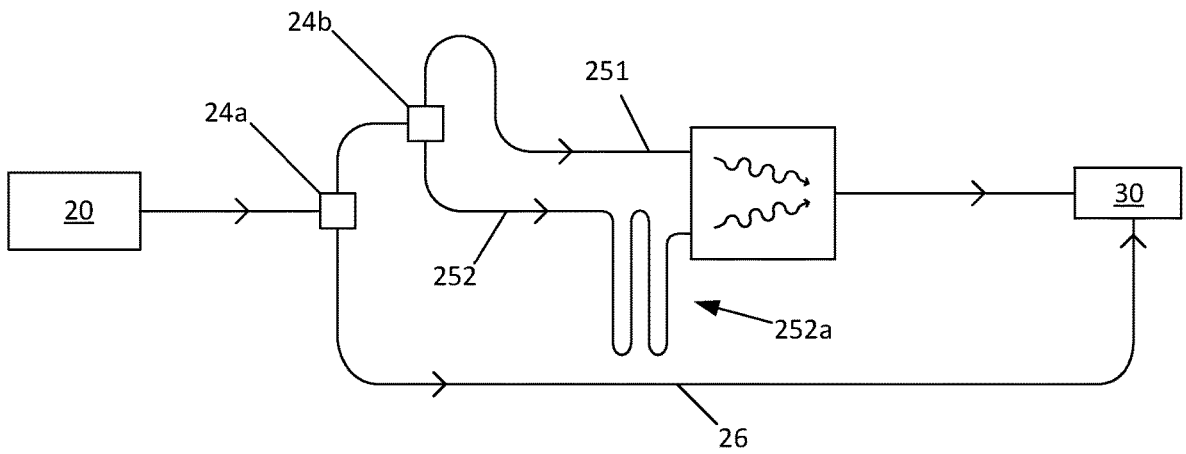

FIG. 3d shows another example iNIRS system. The iNIRS system of FIG. 3d is similar to that of FIG. 3b. However, in FIG. 3b, a single splitter is shown for splitting light from the light source 20 into each of: (i) a first sample delivery channel 251, (ii) a second sample delivery channel 252, and (iii) a reference channel 26. For iNIRS systems of the present disclosure combining or splitting three or more separate optical channels could be provided by a single component (as shown in FIGS. 1 and 3a to 3c), or this could be provided by multiple components. In FIG. 3d, two light splitters are provided: first light splitter 24a and second light splitter 24b.

The first light splitter 24a is coupled to the light source 20 to receive light therefrom. The first light splitter 24a is arranged to split this light into a sample and reference light channels. The reference channel 26 may extend from the first light splitter 24a towards the detector where it is coupled with a sample receiving channel of the system. The sample light channel extends from the first light splitter 24a to the second light splitter 24b. The second light splitter 24b is provided by a separate component to the first light splitter 24a. The second light splitter 24b is arranged to split the sample light received from the first light splitter 24a into the two sample delivery channels: first sample delivery channel 251 and second sample delivery channel 252 (where the second sample delivery channel 252 has additional optical channel length 252a as described herein). It is to be appreciated that a similar arrangement could be provided for example systems in which two sample receiving channels are first combined into a single sample channel, and that single sample channel is then combined with the reference channel (e.g. by a separate component), and/or in which one sample receiving channel is combined with the reference channel before the other sample receiving channel is then combined with that combined channel.

Figure 3E:
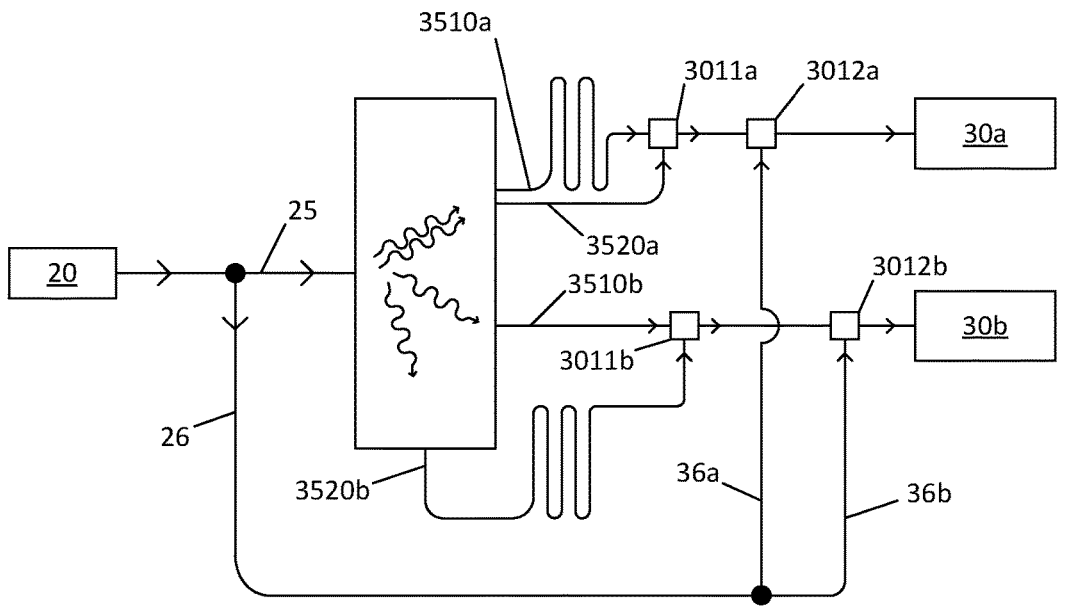

FIG. 3e shows another example iNIRS system. The system of FIG. 3e includes two detectors: first detector 30a and second detector 30b. For simplicity, light combiners of each detector are shown as separate components to the detector, but it will be appreciated that these light combiners may form part of the detector. One light source 20 is shown in FIG. 3e. Light from the light source 20 is split onto both: (i) sample delivery channel 25 for delivering sample light towards the object to be imaged, and (ii) reference delivery channel 26 for providing reference light to the detectors 30a, 30b. Each of the detectors 30a, 30b has an associated reference receiving channel 36a, 36b respectively. Each reference receiving channel 36a, 36b is arranged for providing light from the reference channel 26 to its respective detector. For example, the reference channel 26 may have a light splitter for splitting reference light from the reference channel 26 onto each of the two reference receiving channels 36a, 36b.

Each of the detectors 30a, 30b is coupled to the object to be imaged by two sample receiving channels. As shown, the first detector 30a is coupled to the object by a first detector first sample receiving channel 3510a and a first detector second sample receiving channel 3520a. One of these channels 3510a, 3520a includes an additional optical channel length, as disclosed herein (shown as channel 3510a in FIG. 3e). Likewise, the second detector 30b is coupled to the object by a second detector first sample receiving channel 3510b and a second detector second sample receiving channel 3520b. Again, one of these channels 3510b, 3520b includes an additional optical channel length, as disclosed herein (shown as channel 3520b in FIG. 3e). Thus, as described herein, each of the first and second detectors 30a, 30b may receive first and second sample light, where the time of flight difference between the two sample receiving channels for each detector 30a, 30b is such that the resulting first beat frequencies will have no spectral overlap with the resulting second beat frequencies.

For each of the detectors 30a, 30b, two light combiners are provided: (i) one to combine light from the two sample receiving channels onto a single combined sample channel, and (ii) one to combine light from the single combined sample channel with reference light from the reference receiving channel. Each detector may comprise these two light combiners.

For the first detector 30a, a first detector first combiner 3011a is coupled to both of the first detector sample receiving channels 3510a, 3520a and configured to combine light from those two channels 3510a, 3520a onto a first detector combined sample channel. A first detector second combiner 3012a is coupled to the first reference receiving channel 36a and the first detector combined sample channel to combine the combined sample light with the reference light. The first detector 30a is coupled to the first detector second combiner 3012a to receive the combined light therefrom. For the second detector 30b, a second detector first combiner 3011b is coupled to both of the second detector sample receiving channels 3510b, 3520b and configured to combine light from those two channels 3510b, 3520b onto a second detector combined sample channel. A second detector second combiner 3012b is coupled to the second reference receiving channel 36b and the second detector combined sample channel to combine the combined sample light with the reference light. The second detector 30b is coupled to the second detector second combiner 3012b to receive the combined light therefrom. As such, the combining of different light may be provided in stages (e.g. by a plurality of different components).

FIG. 3e also illustrates different example functionality for this iNIRS system. As described herein, each detector is configured to receive and process first and second sample light data. Each detector may therefore effectively obtain information pertaining to two (or more) different photon distributions for sample light passing through the object to be imaged. For example, one digitiser channel could be used for each detector, and the resulting data obtained from that digitiser channel may be indicative of two different beat frequency distributions (i.e. it may contain a first sample light photon distribution and a second sample light photon distribution). In other words, iNIRS systems of the present disclosure may be arranged to better utilise the full bandwidth of a digitiser channel (e.g. to obtain more useable data per each digitiser channel). Sample delivery channels and/or sample receiving channels may be arranged on the object so that the system is configured to obtain two or more photon distributions for a similar volume within the object and/or so that at least some obtained photon distributions are for different volumes within the object.

As one example, as shown in FIG. 3*e*, the sample receiving channels 3510*a*, 3520*a* of the first detector 30*a* may be co-located on the object. That is, the two may be located adjacent to each other (e.g. within a threshold distance of each other). As such, on average, sample light photons travelling from the sample delivery channel 25 to the two sample receiving channels 3510*a*, 3520*a* of the first detector 30*a* may travel through a substantially similar volume of the object (e.g. as shown by the photon paths in FIG. 3*e*). In other words, sample light passing through each of these sample receiving channels for the first detector 30*a* may effectively be used for imaging the same region of the object. The first detector 30*a* may thus effectively be simultaneously obtaining two (or more) photon distributions for the same region of the object (e.g. using a single digitiser channel). The system may be configured to process the different photon distributions together, such as to average data obtained from each distribution (i.e. to average based on distributions obtained using both sample receiving channels).

As another example, as shown in FIG. 3*e*, the sample receiving channels 3510*b*, 3520*b* of the second detector 30*b* may be spaced apart on the object. In which case, the same detector (second detector 30*b*) could be used to simultaneously image two different volumes within the object. As shown in FIG. 3*e*, the sample light photons being received at each channel may, on average, travel through a substantially different volume within the image. As such, a first sample photon distribution may represent one portion of the object, whereas a second sample photon distribution may represent a different portion of the object.

It is to be appreciated in the context of the present disclosure that the different examples may be combined with each other. For example, an iNIRS system may be provided in which there are two sample delivery channels (of different lengths) and two sample receiving channels (of different lengths). These channels may be arranged (e.g. of selected lengths) so that all of the combinations of different sample light channel paths will fit in their own region on the resulting interferogram. That is, the channels may be arranged to stack all of the different beat frequency distributions within one interferogram without spectral overlap between the distributions. Similarly, multiple sources may be used where some, or all, of those sources are coupled to the object via two or more sample delivery channels. Likewise, there may be three or more sample delivery channels and/or sample receiving channels.

The present disclosure may therefore provide iNIRS systems in which sample light may travel from source to object, and from object to detector, along two or more different optical paths (irrespective of the path taken through the object between the sample delivery channel and the sample receiving channel). These different optical paths may be of different lengths such that resulting beat frequency distributions for the different combinations of sample and reference light may fit on the same interferogram without spectral overlap. As such, one digitiser channel of an ADC may be used to digitise one interferogram, where that one interferogram contains information indicative of two or more different DTOFs for sample light. This arrangement may enable more imaging data to be obtained for the object. In other words, this arrangement may enable more data to be obtained without needing to increase the number of digitisers in the system. For example, iNIRS systems of the present disclosure may be arranged to maximise the number of different beat frequency distributions provided within one interferogram to be digitised. That is, for a given digitiser bandwidth, the iNIRS system may be arranged with the maximum number of different distributions present in one interferogram without spectral overlap between those distributions in that interferogram.

In each of the examples described herein, each interferogram may provide an indication of all of the sample light photons which were incident on the detector 30 at a given moment in time. Within that interferogram, there may be two or more different beat frequency distributions associated with different sample light incident on the detector (first/second etc.). A controller may be configured to extract a DTOF for each of these sample light beat frequency distributions. Each said determined DTOF may provide a distribution showing the time of flight for all relevant sample light photons which were incident on the light detector 30 at a given moment in time. Each DTOF may contain an ensemble average representing a large number of incident photons (in each of a plurality of different TOF bins). The intensity for each TOF bin will provide an indication of the number of incident photons at that TOF. A phase of a TOF bin (e.g. obtained using a Fourier analysis) may represent an average phase for all of the photons arriving in that TOF bin. As described in more detail below, numerous properties of the subject's brain tissue may be determined based on such DTOF data obtained for the subject's brain tissue.

The iNIRS system 10 may be configured to obtain a plurality of time-ordered DTOFs for the light detector 30. This may include averaged DTOFs (where the simultaneously obtained first and second sample light DTOFs were averaged). The digitiser may provide a digital output indicative of the different measurements, and this digital output may optionally be processed in a number of ways to provide and/or use such DTOF data. Examples of such steps will now be described.

The controller 40 may be configured to receive raw digital interferogram data (e.g. data representative of the interferogram obtained by converting the combined light signal into digital data). This raw interferogram may be divided into individual sweeps for the wavelength swept emission from the light source 20. For example, the sweep rate of the light source 20 and a time at which the first sweep commenced may be used to determine the sweep cycles. The data may then be divided into groups, where each group represents an individual sweep. An optional Hilbert transform may be performed on the data at this stage. Data windowing may be performed (e.g. with a Hann or Blackman-Harris window) to reduce sidelobes in the data. A Fourier analysis may be performed on the data, either inverse or normal. For instance, an inverse Fourier Transform may be performed. The Fourier analysis may be performed for each wavelength sweep of the light source 20. The resulting data may be in the form of a series of Temporal Point Spread Functions ('TPSF'), with each TPSF corresponding to an associated wavelength sweep. The TPSF data may be processed to remove an Instrument Response Function ('IRF') therefrom to provide the DTOF data. For example, the IRF may be filtered out (e.g. deconvolved and/or subtracted) using postprocessing.

In other words, the iNIRS system 10 may be configured to determine a time-ordered series of time of flight distributions for sample light photons incident on one or more detectors. Where the object to be imaged is a subject's brain, this DTOF data may be processed to provide information relating to a number of different physical properties of the subject's brain tissue. The DTOF data may be used to determine optical properties of the medium through which the sample light has travelled. Each TOF bin in a DTOF may represent a selected volume within the subject's brain, and each DTOF represents a total volume of tissue probed by the photons (e.g. each DTOF may represent a weighted average of properties of the brain tissue, as well as other tissues through which the photons have travelled such as scalp, skull etc.). The optical properties include scattering and absorption properties for the subject's brain tissue. The DTOF data may be used to determine dynamic properties of the subject's brain tissue, such as how particular properties vary over time. This includes how the optical properties evolve over time, as well as properties indicative of movement within the subject's brain tissue (e.g. due to the flow of blood).

The controller 40 may store data which correlates time of flight for a sample light photon (or for a TOF bin) to an indication of average path trajectory for that photon. This may include an indication of the depth of the penetration into the subject's brain tissue for that photon, and/or an indication of the region(s) of the subject's brain tissue through which that photon travelled from light source 20 to light detector 30. The controller 40 may be configured to process the DTOF data by dividing this data up into selected TOF bins. Within each TOF bin, the data may provide depth-resolved evolution data for the subject's brain tissue. That is, as the TOF may be associated with certain penetration depths or regions, each TOF bin may contain data showing properties associated with a certain penetration depth or region. The evolution of data within each TOF bin may therefore provide an indication of how one or more properties of the subject's brain tissue are evolving. For example, where the evolution suggests a change in movement (e.g. a flow of blood), that movement may be identified, as may the region in which that movement is occurring. For this, a TOF-resolved decay slope may be used to identify how the curve is decaying over time for specific TOFs (e.g. for specific penetration depths/regions).

In other words, the iNIRS system 10 may be configured to perform an autocorrelation in which DTOFs for successive wavelength sweeps are combined to assess fluctuations in the light field at the light detector 30 over time. The fluctuations may be quantified due to relevant fluctuations in DTOFs over time. The fluctuations may also be depth-resolved, by identifying the relevant TOFs at which those fluctuations are occurring (and thus the relevant penetration depths/regions). The controller 40 may be configured to process the data received from the light detector(s) 30 to provide time of flight information with depth-resolved auto-correlations for the subject's brain tissue. The controller 40 may be configured to use this information to obtain an indication of a plurality of different properties of the subject's brain tissue, such as intracranial pressure ('ICP'), blood flow index, artery elasticity, etc. These properties of the subject's brain tissue may be used for a plurality of different forms of neuroimaging and analysis, such as in a brain-computer interface, for imaging regions of the brain to identify potential localised injury or strokes, and/or to monitor neuro responses to substances, such as drugs.

As will be appreciated in the context of the present disclosure, when a square-law detector is used, the intensity at the detector may be proportional to the square of the summed electric field intensity. The rate of change of the optical frequency multiplied by time delay may give rise to a frequency of the interference fringes present in each interferogram. In other words, a Fourier Transformed interferogram containing a plurality of beat frequencies may be used to indicate the photon time of flights associated with those beat frequencies present in the interferogram. In other words, the iNIRS system 10 is arranged to measure a phase or frequency shift between photons of light in the two inputs to the detector (reference and sample), and to attribute such differences to properties of the intervening brain tissue for the sample light.

For this, the light detector 30 may comprise a light combiner arranged to combine the received light, and to provide said combined light (which includes the components of first and/or second sample light at different beat frequencies) to signal processing circuitry. The detector 30 may be configured to create an interference pattern based on the difference in optical frequencies between the incident sample and reference electric fields, e.g. wherein the intensity or power detected is proportional to the square of the incident electric field and the incident electric field is the sum of the sample and reference electric fields. The intensity or power detected (in the form of a photocurrent) may therefore be equal to the square of the sum of the incident sample and reference electric fields. Such detectors may comprise photodiodes, avalanche photodiodes and/or fast linescan cameras, streak cameras and fast CCD or CMOS sensors. The detector 30 may be a high bandwidth detector. For example, the detector 30 may be configured to resolve interference fringes at 100 Mhz or more, such as up to 1 GHz. The detector 30 may comprise a single speckle detector. For example, optical fibres used in the detector may be single mode. If a multi-mode detector is used, then the detector may comprise an array of square-law detectors, such as a photodiode array, focal plane array, fast linescan camera or fast CCD array. The detector may also comprise a balanced detector array. The balanced detector array may be configured so that the reference light and the scattered light are combined and split (e.g. evenly) onto a pair of out-of-phase detectors such as with a 4-port (2-in, 2-out 50:50 ratio) fibre coupler or a beamsplitter cube. A balanced detector may enhance signal to noise of the detected signal by rejecting incoherent portions of the signal. The balanced photodetector may also fully utilise all light transmitted through the interferometer and suppress common noise, such as laser intensity noise.

It will be appreciated in the context of the present disclosure that examples described herein are not intended to be limiting. Instead, examples describe certain potential ways of implementing the claimed technology. For example, the iNIRS system 10 is described with a series of optical cables providing channels and probes for coupling those channels to the subject's scalp. However, it will be appreciated that the probes themselves may be part of the optical channels, or probes may not be provided at all. Similarly, the arrangement of reference channels is just intended to show that reference light is delivered from the light source to the light detectors via optical channels (rather than via the subject's brain tissue). For example, where multiple light sources are provided, each light source may include one reference channel for each light detector, where that reference channel directly connects the light source to the light detector. In which case, there may be no reference connections in the system at all. Additionally, or alternatively, where multiple light sources are used, reference light may be transmitted on a common reference optical channel, where some of that reference light is taken from the common reference optical channel to each of the optical detectors. The light source may also be arranged to deliver light to one of a plurality of different locations on the subject's scalp. For example, the light source may be coupled to a plurality of different sample delivery channels, each extended towards the subject's scalp (e.g. from a light splitter).

It will be appreciated that the particular arrangement shown for signal processing circuitry of the detector need not be considered limiting. Each light detecting arrangement may be configured to combine first sample, second sample light and reference light to provide combined light signals with components at one or more first beat frequencies and one or more second beat frequencies, and to process those combined light signals to determine one or more properties of the subject's brain tissue. Any suitable signal processing and/or conversion circuitry could be used for this. For example, a transimpedance amplifier may not be needed (e.g. depending on the photodetector or ADC, no current to voltage conversion may be needed, or this may be performed in a different way). Similarly, a balanced photodetector need not be used, and instead a single photodetector, such as a photodiode, could be used. Similarly, the arrangement with the ADC shown in the Figs. need not be considered limiting. For example, multiple ADCs may be used (e.g. one for each detector output stream), or all detector output streams may be fed into one common ADC.

It will be appreciated from the discussion above that the examples shown in the figures are merely exemplary, and include features which may be generalised, removed or replaced as described herein and as set out in the claims. With reference to the drawings in general, it will be appreciated that schematic functional block diagrams are used to indicate functionality of systems and apparatus described herein. In addition the processing functionality may also be provided by devices which are supported by an electronic device. It will be appreciated however that the functionality need not be divided in this way, and should not be taken to imply any particular structure of hardware other than that described and claimed below. The function of one or more of the elements shown in the drawings may be further subdivided, and/or distributed throughout the apparatus of the disclosure. In some examples the function of one or more elements shown in the drawings may be integrated into a single functional unit.

As will be appreciated by the skilled reader in the context of the present disclosure, each of the examples described herein may be implemented in a variety of different ways. Any feature of any aspects of the disclosure may be combined with any of the other aspects of the disclosure. For example method aspects may be combined with apparatus aspects, and features described with reference to the operation of particular elements of apparatus may be provided in methods which do not use those particular types of apparatus. In addition, each of the features of each of the examples is intended to be separable from the features which it is described in combination with, unless it is expressly stated that some other feature is essential to its operation. Each of these separable features may of course be combined with any of the other features of the examples in which it is described, or with any of the other features or combination of features of any of the other examples described herein. Furthermore, equivalents and modifications not described above may also be employed without departing from the invention.

Certain features of the methods described herein may be implemented in hardware, and one or more functions of the apparatus may be implemented in method steps. It will also be appreciated in the context of the present disclosure that the methods described herein need not be performed in the order in which they are described, nor necessarily in the order in which they are depicted in the drawings. Accordingly, aspects of the disclosure which are described with reference to products or apparatus are also intended to be implemented as methods and vice versa. The methods described herein may be implemented in computer programs, or in hardware or in any combination thereof. Computer programs include software, middleware, firmware, and any combination thereof. Such programs may be provided as signals or network messages and may be recorded on computer readable media such as tangible computer readable media which may store the computer programs in non-transitory form. Hardware includes computers, hand-held devices, programmable processors, general purpose processors, application specific integrated circuits (ASICs), field programmable gate arrays (FPGAs), and arrays of logic gates.

Any controller of the present disclosure may be implemented with fixed logic such as assemblies of logic gates or programmable logic such as software and/or computer program instructions executed by a processor. The controller may comprise a central processing unit (CPU) and associated memory, connected to a graphics processing unit (GPU) and its associated memory. Other kinds of programmable logic include programmable processors, programmable digital logic (e.g., a field programmable gate array (FPGA), a tensor processing unit (TPU), an erasable programmable read only memory (EPROM), an electrically erasable programmable read only memory (EEPROM), an application specific integrated circuit (ASIC), or any other kind of digital logic, software, code, electronic instructions, flash memory, optical disks, CD-ROMs, DVD ROMs, magnetic or optical cards, other types of machine-readable mediums suitable for storing electronic instructions, or any suitable combination thereof. In particular, any controller of the present disclosure may be provided by an ASIC.

Other examples and variations of the disclosure will be apparent to the skilled addressee in the context of the present disclosure.

The invention claimed is:

1. An interferometric near infrared spectroscopy, iNIRS, system comprising:

a light emitting arrangement comprising a light source configured to provide wavelength swept emission of light; and a light detecting arrangement comprising an interferometric optical detector;

the iNIRS system comprising a plurality of optical channels arranged to define:

a first optical channel path arranged to extend: (i) between the light source and the object for delivering first sample light from the light source to the object, and (ii) between the object and the detector for delivering first sample light received from the object to the detector;

a second optical channel path arranged to extend: (i) between the light source and the object for delivering second sample light from the light source to the object, and (ii) between the object and the detector for delivering second sample light received from the object to the detector; and a reference optical channel path arranged to extend between the light source and the detector for delivering reference light from the light source to the detector along a reference channel;

wherein the detector is arranged to combine:

the reference light with the first sample light to provide light signals at a plurality of first beat frequencies between the first sample light and the reference light; and the reference light with the second sample light to provide light signals at a plurality of second beat frequencies between the second sample light and the reference light;

wherein the first optical channel path is of a different length to the second optical channel path to inhibit spectral overlap between the first and second beat frequencies.

2. The iNIRS system of claim 1, wherein a portion of the first optical channel path shares a common optical channel with a portion of the second optical channel path.

3. The iNIRS system of claim 2, wherein the common optical channel couples either: (i) the light source to the object, or (ii) the object to the detector.

4. The iNIRS system of claim 1, wherein the plurality of optical channels comprises:

a sample delivery channel coupled to the light source and arranged to be coupled to the object for directing first and second sample light from the light source towards the object;

a first sample receiving channel arranged to be coupled to the object for receiving first sample light therefrom; and a second sample receiving channel arranged to be coupled to the object for receiving second sample light therefrom;

wherein the first optical channel path comprises the sample delivery channel and the first sample receiving channel;

wherein the second optical channel path comprises the sample delivery channel and the second sample receiving channel; and wherein the first sample receiving channel is of a different length to the second sample receiving channel, thereby to provide a difference in length between the first optical channel path and the second optical channel path.

5. The iNIRS system of claim 1, wherein the iNIRS system comprises an analogue to digital converter, ADC, configured to obtain sample data containing an indication of the first and second beat frequencies detected by the optical detector.

6. The iNIRS system of claim 5, wherein the iNIRS system is configured to use a single ADC channel to obtain the sample data for both the first and second beat frequencies.

7. The iNIRS system of claim 5, wherein the system comprises a controller configured to process the sample data to obtain: (i) first sample data containing an indication of the first beat frequencies detected by the optical detector, and (ii) second sample data containing an indication of the second beat frequencies detected by the optical detector.

8. The iNIRS system of claim 7, wherein processing the sample data comprises separating the first sample data from the second sample data based on an indication of beat frequency.

9. The iNIRS system of claim 8, wherein the controller is configured to process the sample data so that: (i) the first sample data contains detected beat frequencies at below a threshold frequency, and (ii) the second sample data contains detected beat frequencies at above the threshold frequency.

10. The iNIRS system of claim 7, wherein the controller is configured to obtain: (i) first time of flight data for the first sample light based on the first sample data, and (ii) second time of flight data for the second sample light based on the second sample data.

11. The iNIRS system of claim 10, wherein the controller is configured to average the first time of flight data and the second time of flight data to provide combined time of flight data.

12. The iNIRS system of claim 10, wherein the controller is configured to align the first time of flight data with the second time of flight data based on a temporal offset associated with the difference in length between the first optical channel path and the second optical channel path.

13. The iNIRS system of claim 12, wherein aligning the first time of flight data with the second time of flight data comprises at least one of: (i) applying a fixed temporal offset associated with the difference in duration of time taken for light to travel along the first and second optical channel paths, and (ii) applying a temporal offset based on aligning one or more features in the first time of flight data with corresponding features in the second time of flight data.

14. The iNIRS system of claim 1, wherein the difference in length between the first and second optical channel paths is at least as large as a distance corresponding to an expected temporal width for a distribution of time of flight, DTOF, associated with the first sample light.

15. The iNIRS system of claim 1, wherein the iNIRS system comprises a plurality of optical channels arranged to define three or more optical channel paths arranged to extend: (i) between the light source and the object, and (ii) between the object and the detector, and wherein each of the optical channel paths are of different lengths to each other to inhibit spectral overlap between beat frequencies associated therewith.

16. The iNIRS system of claim 1, wherein the light detecting arrangement is a first light detecting arrangement, and the iNIRS system comprises a second light detecting arrangement, the second light detecting arrangement comprising a second detector, wherein the plurality of optical channels are arranged to define:

a third optical channel path arranged to extend: (i) between the light source and the object for delivering third sample light from the light source to the object, and (ii) between the object and the second detector for delivering third sample light received from the object to the second detector;

a fourth optical channel path arranged to extend: (i) between the light source and the object for delivering fourth sample light from the light source to the object, and (ii) between the object and the second detector for delivering fourth sample light received from the object to the second detector; and a second reference optical channel path arranged to extend between the light source and the second detector for delivering reference light from the light source to the second detector along a second reference channel;

wherein the second detector is arranged to combine:

the reference light with the third sample light to provide light signals at a plurality of third beat frequencies between the third sample light and the reference light; and the reference light with the fourth sample light to provide light signals at a plurality of fourth beat frequencies between the fourth sample light and the reference light;

wherein the third optical channel path is of a different length to the fourth optical channel path to inhibit spectral overlap between the third and fourth beat frequencies.

17. The iNIRS system of claim 1, wherein the plurality of optical channels comprises:

a first sample delivery channel coupled to the light source and arranged to be coupled to the object for directing first sample light from the light source towards the object;

a second sample delivery channel coupled to the light source and arranged to be coupled to the object for directing second sample light from the light source towards the object; and a sample receiving channel arranged to be coupled to the object for receiving first and second sample light therefrom;

wherein the first optical channel path comprises the first sample delivery channel and the sample receiving channel;

wherein the second optical channel path comprises the second sample delivery channel and the sample receiving channel; and wherein the first sample delivery channel is of a different length to the second sample delivery channel, thereby to provide a difference in length between the first optical channel path and the second optical channel path.

18. The iNIRS system of claim 1, wherein the plurality of optical channels comprises:

a first sample delivery channel coupled to the light source and arranged to be coupled to the object for directing light from the first light source towards the object;

a second sample delivery channel coupled to the light source and arranged to be coupled to the object for directing light from the second light source towards the object;

a first sample receiving channel arranged to be coupled to the object for receiving therefrom first sample light from the first sample delivery channel and first sample light from the second sample delivery channel; and a second sample receiving channel arranged to be coupled to the object for receiving therefrom second sample light from the first sample delivery channel and second sample light from the second sample delivery channel;

wherein the first sample delivery channel is of a different length to the second sample delivery channel, and the first sample receiving channel is of a different length to the second sample receiving channel to inhibit spectral overlap between each of: (i) first beat frequencies for first sample light from the first sample delivery channel, (ii) first beat frequencies for first sample light from the second sample delivery channel, (iii) second beat frequencies for second sample light from the first sample delivery channel, and (iv) second beat frequencies for second sample light from the second sample delivery channel.

19. An interferometric near infrared spectroscopy, iNIRS, system comprising:

a light emitting arrangement comprising:

a light source configured to provide wavelength swept emission of light;

a sample delivery channel coupled to the light source and arranged to be coupled to an object for directing light from the light source towards the object; and a reference channel coupled to the light source for receiving light therefrom;

a light detecting arrangement comprising:

a first sample receiving channel arranged to be coupled to the object for receiving first sample light therefrom;

a second sample receiving channel arranged to be coupled to the object for receiving second sample light therefrom, the first and second sample light each comprising light emitted from the light source; and an interferometric optical detector coupled to: (i) the first sample receiving channel for receiving first sample light, (ii) the second sample receiving channel for receiving second sample light, and (iii) the reference channel for receiving reference light, and wherein the optical detector is arranged to combine:

the reference light with the first sample light to provide light signals at a plurality of first beat frequencies between the first sample light and the reference light; and the reference light with the second sample light to provide light signals at a plurality of second beat frequencies between the second sample light and the reference light;

wherein the first sample receiving channel is of a different length to the second sample receiving channel to inhibit spectral overlap between the first and second beat frequencies.

20. An interferometric near infrared spectroscopy, iNIRS, system comprising:

a light emitting arrangement comprising:

a light source configured to provide wavelength swept emission of light;

a first sample delivery channel coupled to the light source and arranged to be coupled to an object for directing light from the light source towards the object;

a second sample delivery channel coupled to the light source and arranged to be coupled to the object for directing light from the light source towards the object; and a reference channel coupled to the light source for receiving light therefrom;

a light detecting arrangement comprising:

a sample receiving channel arranged to be coupled to the object for receiving first and second sample light therefrom, the first sample light comprising light emitted from the light source which travelled along the first sample delivery channel and the second sample light comprising light emitted from the light source which travelled along the second sample delivery channel; and an interferometric optical detector coupled to: (i) the sample receiving channel for receiving first and second sample light, and (ii) the reference channel for receiving reference light, and wherein the optical detector is arranged to combine:

the reference light with the first sample light to provide light signals at a plurality of first beat frequencies between the first sample light and the reference light; and the reference light with the second sample light to provide light signals at a plurality of second beat frequencies between the second sample light and the reference light;

wherein the first sample delivery channel is of a different length to the second sample delivery channel to inhibit spectral overlap between the first and second beat frequencies.

* * * * *